United States Patent
Agaian et al.

(10) Patent No.: US 10,055,551 B2
(45) Date of Patent: Aug. 21, 2018

(54) SYSTEMS AND METHODS FOR QUANTITATIVE ANALYSIS OF HISTOPATHOLOGY IMAGES USING MULTICLASSIFIER ENSEMBLE SCHEMES

(71) Applicants: BOARD OF REGENTS, THE UNIVERSITY OF TEXAS SYSTEM, Austin, TX (US); STANFORD UNIVERSITY, Stanford, CA (US)

(72) Inventors: Sos Agaian, San Antonio, TX (US); Clara M. Mosquera-Lopez, San Antonio, TX (US); Aaron Greenblatt, Portola Valley, CA (US)

(73) Assignee: Board of Regents of the University of Texas System, Austin, TX (US)

( * ) Notice: Subject to any disclaimer, the term of this patent is extended or adjusted under 35 U.S.C. 154(b) by 175 days.

(21) Appl. No.: 15/028,314

(22) PCT Filed: Oct. 10, 2014

(86) PCT No.: PCT/US2014/060178
§ 371 (c)(1),
(2) Date: Apr. 8, 2016

(87) PCT Pub. No.: WO2015/054666
PCT Pub. Date: Apr. 16, 2015

(65) Prior Publication Data
US 2016/0253466 A1   Sep. 1, 2016

Related U.S. Application Data

(60) Provisional application No. 61/889,448, filed on Oct. 10, 2013, provisional application No. 61/907,325, filed on Nov. 21, 2013.

(51) Int. Cl.
*G06K 9/00* (2006.01)
*G06F 19/00* (2018.01)
(Continued)

(52) U.S. Cl.
CPC ........ *G06F 19/345* (2013.01); *G06K 9/0014* (2013.01); *G06K 9/34* (2013.01);
(Continued)

(58) Field of Classification Search
None
See application file for complete search history.

(56) References Cited

U.S. PATENT DOCUMENTS

| 6,269,351 B1 | 7/2001 | Black |
| 6,463,438 B1 | 8/2002 | Veltri et al. |

(Continued)

FOREIGN PATENT DOCUMENTS

| EP | 0 461 902 | 12/1991 |
| EP | 1286280 | 2/2003 |

(Continued)

OTHER PUBLICATIONS

Doyle, Scott, et al. "A boosted Bayesian multiresolution classifier for prostate cancer detection from digitized needle biopsies." IEEE transactions on biomedical engineering 59.5 (2012): 1205-1218. (Year: 2012).*

(Continued)

*Primary Examiner* — Nirav G Patel
(74) *Attorney, Agent, or Firm* — Meyertons, Hood, Kivlin, Kowert & Goetzel, P.C.; Mark R. DeLuca

(57) ABSTRACT

Described herein are systems and methods for performing multi-stage detection and classification of cancer regions from digitized images of biopsy slides. Novel methods for processing the digitized images to improve feature extraction and structure identification are disclosed, including but not limited to the use of quaternions, logarithmic mappings of color channels, and application of wavelets to logarithmic color channel mappings. The extracted features are utilized in improved machine learning algorithms that are further (Continued)

optimized to analyze multiple color channels in multiple dimensions. The improved machine learning algorithms include techniques for accelerating the training of the algorithms, making their application to biopsy detection and classification practical for the first time. The performance of the described systems and methods are further improved by the disclosure of a novel multistage machine learning scheme, in which additional classifiers are utilized to choose among the classes proposed by other classifiers in close cases.

19 Claims, 9 Drawing Sheets

(51) Int. Cl.
G16H 50/20 (2018.01)
G06N 3/04 (2006.01)
G06N 5/04 (2006.01)
G06N 99/00 (2010.01)
G06K 9/62 (2006.01)
G06T 7/00 (2017.01)
G06K 9/34 (2006.01)
G06K 9/46 (2006.01)
G06K 9/66 (2006.01)
G06T 7/246 (2017.01)

(52) U.S. Cl.
CPC ........... *G06K 9/4652* (2013.01); *G06K 9/628* (2013.01); *G06K 9/629* (2013.01); *G06K 9/6212* (2013.01); *G06K 9/66* (2013.01); *G06N 3/0427* (2013.01); *G06N 5/043* (2013.01); *G06N 99/005* (2013.01); *G06T 7/0012* (2013.01); *G06T 7/0014* (2013.01); *G06T 7/246* (2017.01); *G16H 50/20* (2018.01); *G06K 2009/4666* (2013.01); *G06T 2207/10024* (2013.01); *G06T 2207/10056* (2013.01); *G06T 2207/20036* (2013.01); *G06T 2207/20064* (2013.01); *G06T 2207/20081* (2013.01); *G06T 2207/20084* (2013.01); *G06T 2207/30024* (2013.01); *G06T 2207/30096* (2013.01)

(56) References Cited

U.S. PATENT DOCUMENTS

| | | | |
|---|---|---|---|
| 7,483,554 | B2 | 1/2009 | Kotsianti et al. |
| 7,761,240 | B2 | 7/2010 | Saidi et al. |
| 7,899,625 | B2 | 3/2011 | Bhanot et al. |
| 8,139,831 | B2 | 3/2012 | Khamene et al. |
| 2002/0165837 | A1 | 11/2002 | Zhang et al. |
| 2004/0258310 | A1 | 12/2004 | Giger et al. |
| 2006/0064248 | A1 | 2/2006 | Saidi et al. |
| 2007/0019854 | A1 | 1/2007 | Gholap et al. |
| 2008/0130883 | A1* | 6/2008 | Agaian ............... G06T 1/0028 380/54 |
| 2008/0205518 | A1 | 8/2008 | Wilinski et al. |
| 2009/0077543 | A1 | 3/2009 | Siskind et al. |
| 2009/0161928 | A1 | 6/2009 | Khamene et al. |
| 2009/0274386 | A1 | 11/2009 | Panetta et al. |
| 2009/0297007 | A1 | 12/2009 | Cosatto et al. |
| 2010/0054622 | A1 | 3/2010 | Adams |
| 2010/0088264 | A1 | 4/2010 | Teverovskiy et al. |
| 2010/0098306 | A1 | 4/2010 | Madabhushi et al. |
| 2010/0177950 | A1 | 7/2010 | Donovan et al. |
| 2010/0312072 | A1 | 12/2010 | Breskin |
| 2011/0243417 | A1 | 10/2011 | Madabhushi et al. |
| 2012/0116716 | A1 | 6/2012 | Lokshin et al. |
| 2012/0148141 | A1 | 6/2012 | Ozcan et al. |
| 2017/0220893 | A1* | 8/2017 | Siddiqui ............... G06K 9/4628 |

FOREIGN PATENT DOCUMENTS

| | | |
|---|---|---|
| KR | 100989650 | 10/2010 |
| WO | 2009006696 | 1/2009 |
| WO | 2013049153 | 4/2013 |

OTHER PUBLICATIONS

Cheng, Heng-Da, et al. "Automated breast cancer detection and classification using ultrasound images: A survey." Pattern recognition 43.1 (2010): 299-317. (Year: 2010).*
International Search Report and Written Opinion for PCT Application No. PCT/US2014/060178 dated Feb. 25, 2015.
International Preliminary Report on Patentability for PCT Application No. PCT/US2014/060178 dated Apr. 12, 2016.
International Search Report/Written Opinion for PCT Application No. PCT/US2012/057264 dated Apr. 24, 2013.
International Preliminary Report on Patentability for PCT Application No. PCT/US2012/057264 dated Apr. 1, 2014.
Agaian "Visual Morphology", Proc. SPIE, (3646), 139-150 (1999).
Agaian et al. "A new edge detection algorithm in image processing based on LIP-ratio approach", Proc. SPIE, vol. 7532, (2010).
Basavanhally et al. "EM-based segmentation-driven color standardization of digitized histopathology," in Proc. SPIE Medical Imaging, 2013.
Bautista et al. "Color standardization in whole slide imaging using a color calibration slide," Journal of pathology informatics, vol. 5, 2014.
Bejnordi et al. "Quantitative analysis of stain variability in histology slides and an algorithm for standardization," in SPIE Medical Imaging. International Society for Optics and Photonics, 2014, pp. 904 108.
Bezdek "Cluster validity with fuzzy sets," J. of Cybern., vol. 3, pp. 58-71, 1974.
Chang et al. "Texture Analysis and Classification with Tree-Structured Wavelet Transform", IEEE Trans. Image Process, vol. 2, No. 4, pp. 429-441(1993).
Deng et al. "Differentation-based edge detection using the logarithmic image processing model". Journal of Mathematical Imaging and Vision 8, 161-180 (1998) (Abstract).
Deng et al. "The logarithmic image processing model and its applications", IEEE Proc. of the 27th Asilomar Conference on Signals, Systems, and Computers (ACSSC93), 2, 1047-1041(1993).
Dikbas et al. "Chrominance Edge preserving Grayscale Transformation with Approximate First Principal Component for Color Edge Detection", IEEE Proc. ICIP 2007, II,261-264, 2007.
Ding et al. "On the canny edge detector". Pattern Recognition. vol. 34, Issue 3, pp. 721-725 Mar. 2001.
Dony et al. "Edge detection on color images using RGBvector angles", IEEE Proc. of the 1999 IEEE Canadian Conference on Electrical and Computer Engineering Shaw Conference Center, Edmonton, Alberta, Canada , 1999.
Doyle et al "Automated grading of prostate cancer using architectural and textural image features", IEEE International Symposium on Biomedical Imaging: From Nano to Macro ISBI 2007, pp. 1284-1287,2007.
Felsberg "A Novel two-step method for CT reconstruction," BVM, 2008.
Gao et al. "Color image attribute and quality measurements," in Proc. SPIE Sensing Technology+ Applications, 2014.
Ge et al. A method of Multi-Scale Edge Detection Based on Lifting Scheme and Fusion Rule.Proceedings of 2007 International Conference on wavelet Analysis and Pattern Recognition, Beijing, China Nov. 2-4, 2007.
He et al. "An improved Canny edge detector and its realization of FPGA", IEEE Proc. of the 7th conference on Intelligent Control and Automation, (WCICA2008), 6561-6564, 2008, (Abstract).
Hong-Lei et al. "Road Recognition in High Resolution SAR Image Based on Genetic Algorithm," ICIA,pp. 649-654, IEEE International Conference on Information Acquisition, 2006. (Abstract).

(56) References Cited

OTHER PUBLICATIONS

Huang et al. "Automatic Classification for Pathological Prostate Images Based on Fractal Analysis," IEEE Transactions on Medical Imaging, vol. 28, No. 7, pp. 1037-1050, Jul. 2009.
Huang et al. "Effective Segmentation and Classification for HCC Biopsy Images", Pattern Recognition, vol. 43, No. 4, pp. 1550-1563, 2009. (Abstract).
Jingzhong et al. "A method of edge detection based on improved canny algorithm for the Lidar-depth image", Geoinformatic 2006. SPIE vol. 6419,64190. (Abstract).
Khan et al. "A nonlinear mapping approach to stain normalization in digital histopathology images using image-specific color deconvolution," IEEE Trans. Biomed. Eng., vol. 61, No. 6, pp. 1729-1738, 2014.
Khouzani et al. "Automatic Grading of Pathological Images of Prostate Using Multiwavelet Transform," Proc. IEEE 23rd Annual International Conference, Engineering in Medicine and Biology Society, vol. 3, pp. 2545-2548, 2001.
Khouzani et al. "Multiwavelet grading of pathological images of prostate" Biomedical Engineering, IEEE Transactions on, 2003, vol. 50 (6), 697-704. (Abstract).
Kogan et al. "Visualization using rational morphology and zonal magnitude-reduction", Proc. SPIE, (3304), non linear image processing IX 153-163(1998).
Koschan "A Comparative Study on Color Edge Detecton", IEEE Proc. ACCV'95, Singapore, III. 547-478, 1995.
Laak et al. "Hue-saturation-density (hsd) model for stain recognition in digital images from transmitted light microscopy," Cytometry, vol. 39, No. 4, pp. 275-284, 2000.
Lai et al. "A Harr wavelet approach to compressed image quality measurement", Journal of Visual Communication and Image representation, No. 11, pp. 17-40 (2000).
Lee et al. "Classification for Pathological Prostate Images Based on Fractal Analysis," Proc. IEEE CISP '08, vol. 3, pp. 113-117, May 27-30, 2008.
Lindeberg "Scale-space theory: A basic tool for analyzing structures at different scales," J. of Appl. Statistics, vol. 21, No. 1-2, pp. 225-270, 1994.
Mosquera-Lopez et al. "Exploration of efficacy of gland morphology and architectural features in prostate cancer gleason grading," in IEEE Int. Cont on Syst., Man, and Cybern. (SMC). IEEE, 2012, pp. 2849-2854.
Mosquera-Lopez et al. "The development of a multi-stage learning scheme using new tissue descriptors for automatic grading of prostatic carcinoma," in IEEE Int. Conf. on Acoust., Speech, and Signal Process. (ICASSP). IEEE, 2014.
Mosquera-Lopez et al. "Computer-aided prostate cancer diagnosis from digitized histopathology: A review on texture-based systems," IEEE Reviews in Biomedical Eng., vol. 8, No. 1, pp. 1-16, 2014.
Mosquera-Lopez et al. "A new set of waveletand fractals-based features for gleason grading of prostate cancer histopathology images," in IS&T/SPIE Electron. Imaging. Int. Soc. for Optics and Photonics, 2013, pp. 865 516-865 516-12.
Mosquera-Lopez et al. "Iterative local color normalization using fuzzy image clustering," in Proc. SPIE 8755, 875518, 2013.
Macenko et al. "A method for normalizing histology slides for quantitative analysis," in IEEE International Symposium on Biomedical Imaging: From Nano to Macro (ISBI), vol. 9. Boston, MA: IEEE, 2009, pp. 1107-1110.
Magee et al. "Colour normalisation in digital histopathology images," in Proc. Optical Tissue Image analysis in Microscopy, Histopathology and Endoscopy (MICCAI Workshop), 2009.
Nercessian et al. "A Generalized Set of Kernels for Edge and Line Detection," Proceedings: SPIE Electronic Imaging 2009, San Jose, CA, USA, vol. 7245, 2009. (Abstract).
Nercessian et al. "Multi-scale image fusion using the Parameterized Logarithmic Image Processing model," in Proc. IEEE Systems, Man, and Cybernetics, 2010.

Nercessian et al. "An image similarity measure using enhanced human visual system characteristics," in Proc. SPIE Defense, Security, and Sensing, 2011.
Niethammer et al. "Appearance normalization of histology slides" ser. Lectures notes in Computer Science. Springer, 2010, pp. 58-66.
Oppenheimer "The Pathologic Examination of Prostate Tissue", Phoenix5, 1997, URL: http://www.phoenix5.org/Infolink/oppenpath.html#Tis.
Othman et al. "Colour appearance descriptors for image browsing and retrieval," in Proc. SPIE Electronic Imaging 2008, 2008.
Palomares et al. "General logarithmic image processing convolution", IEEE Transactions on image processing, 15(11), 3602-3608, 2006.
Panetta et al. "Logarithmic edge detection with applications", Journal of computers, 3(9) (2008), 11-19.
Panetta et al. "Human visual system based image enhancement and logarithmic contrast measure", IEEE transactions on systems, man, and cybernetics, part b, 1(38) 174-188(2008).
Panetta et al. "Parameterization of logarithmic image processing models", IEEE Transactions on Systems, Man, and Cybernetics, Part A: Systems and Humans (2007).
Panetta et al. "Techniques for detection and classification of edges in color images", SPIE Proc., vol. 6982, pp. 69820W-69820W-11 (2008).
Panetta "Parameterized logarithmic framework for image enhancement," IEEE Trans. Systems, Man, and Cybernetics, vol. 41, pp. 460-473, 2011.
Pnetta et al. "No reference Color Image Contrast and Quality Measures," IEEE Trans. on Consumer Electronics, vol. 59, No. 3, pp. 643-651, 2013.
Peng et al. "Feature Selection based on Mutual Information: Criteria of Max-Dependency, Max-Relevance, and Min-Redundency", IEEE Transactions on Pattern Analysis and Machine Intelegnce, vol. 21, No. 8, pp. 1226-1237, Aug. 2005.
Phoenix5 "Understanding Gleason Grading", Phoenix 5 with permission from CoMed Communications and Vox Medica, 1997. URL: http://www.phoenix5.org/Infolink/GleasonGrading.html.
Pinoli "The logarithmic image processing model: connections with human brightness perception and contrast estimators", Journal of mathematical image and vision,7(4), 341-358(1997).
Reinhard et al. "Color transfer between images," IEEE Comput. Graph. Appl., vol. 21, No. 5, pp. 34-41, 2001.
Rodriguez et al. "Steganography anomaly detection using simple-one-class classification", Defense and Security Symposium (pp. 65790E-65790E). International Society for Optics and Photonics. (2007).
Roushdy "Comparative study of edge detection algorithms applying on the grayscale noisy image using morphological filter", the International Journal on Graphics, Vision, and Image Processing, 6(4), 17-23 (2006).
Roula et al. "A Multispectral Computer Vision System for Automatic Grading of Prostatic Neoplasia" Proc. IEEE International Symposium on Biomedical Imaging , pp. 193-196, 2002. (Abstract).
Ruzon et al. "Color edge detection with compass operator", IEEE Proc. Conference on Computer Vision andPattern Recognition '99, 2, 160-166, 1999.
Sankar et al. "Fractal Features based on Differential Box Counting Method for the Categorization of Digital Mammograms", International Journal of Computer Information Systems and Industrial Management Applications (IJCISIM), Nov. 7, 2010, vol. 2, pp. 011-019, 2010.
Sarkar et al. "An Efficient Differential Box-Counting Approach to Compute Fractal Dimension of Image", IEEE Trans. on Systems, Man and Cybernetics, vol. 24, No. 1, pp. 115-120, Jan. 1994. (Abstract).
Senanayake et al. "Colour transfer by feature based histogram registration," in British Mack Vision Cont (BMVC). Citeseer, 2007, pp. 1-10.
Sharifi et al. "A Classified and Comparative Study of Edge Detection Algorithms", Proceedings of the Internaional; Conference on information Technology:Coding and Computing (ITCC 2002).

(56) References Cited

OTHER PUBLICATIONS

Shin et al. "Comparison of edge detection algorithms using a structure from motion task," IEEE Transactions on Systems, Man, and Cybernetics, Part B., (4), 589-601 (2001).
Silva et al. "Quantify similarity with measurement of enhancement by entropy," in Proc. SPIE Mobile Multimedia/Image Processing for Military and Security Applications, 2007.
Smith et al. "Similarity Measurement Method for the Classification of Architecturally Differentiated Images" Computers and Biomedical Research vol. 32,No. 1, pp. 1-12, Feb. 1999.
Smith et al. "Effect of pre-processing on binarization", Proc. SPIE, (7534), document recognition and retrieval XVII (2010).
Smith "A tutorial on principal components analysis" Cornell University, USA, (2002), 51, 52.
Stotzka et al. "A hybrid neural and statistical classifier system for histopathologic grading of prostatic lesions" Anal Quant Cytol Histol. (1995); 17(3):204-18. (Abstract).
Tabesh et al. "Automated Prostate Cancer Diagnosis and Gleason Grading of Tissue Microarrays", Proc. SPIE, vol. 6747,pp. 58-70, 2005.
Tabesh et al. "Tumor Classification in Histological Images of Prostate Using Color Texture," Proc. IEEE ACSSC 06, pp. 841-845, Oct.-Nov. 2006.
Tabesh et al. "Multifeature Prostate Cancer Diagnosis and Gleason Grading of Histological Images," IEEE Transactions on Medical Imaging, vol. 26, No. 10, pp. 1366-1378, Oct. 2007.
Tai et al. "Computer-Assisted Detection and Grading of Prostatic Cancer in Biopsy Image", Proc. of the International MultiConference of engineers and Computer scientists IMECS2010, vol. 1, Mar. 17-19, 2010.
Tao et al. "Nonlinear image enhancement to improve face detection in complex lighting environment", International Journal of Computational Intelligence Research, 4(2), 327-336(2006).
Trahanias et al. "Color Edge Detection Using Vector Order Statistics" . IEEE Trans. on image processing, 2(2), 1993.
Wang et al. "An edge detection algorithm based on Canny operator," Intelligent Systems Design and Applications, ISDA 200T Issue , Oct. 20-24, 2007 pp. 623-628. (Abstract).
Wang et al. "Progressive Switching Median Filter for the Removal of Impulse Noise from Highly Corrupted Images". Circuits and Systems II: Analog and Digital Signal Processing, IEEE Transactions on (vol. 46, Issue: 1); 1999, 78-80.
Wang et al. "A universal image quality index," IEEE Signal Processing Letters, pp. 81-84, 2002.
Wesolkowski et al. "Comparison of color image edge detectors in multiple color space". ICIP-2000, 796-799, 2000.
Wetzel et al. "Evaluation of prostate tumor grades by content-based image retrieval" Proc. SPIE 27th AIPR Workshop, (1999); vol. 3584, pp. 244-252. (Abstract).
Vvharton "Comparative study of logarithmic enhancement algorithms with performance measure," in SPIE Electronic Imaging, 2006.
Yagi "Color standardization and optimization in whole slide imaging," Diagnostic Pathology, vol. 6, No. 1, p. S15, 2011.
Ying et al. "Anisotropic filter based modified Canny algorithm,". Fourth International Conference on Fuzzy Systems and Knolwedge Discovery. Aug. 24-27, 2007 vol. 1, on pp. 736-740.
Yu-Qian et al. "Medical images edge detection based on mathematical morphology". Proceedings of the 2005 IEEE, Engineering in Medicine and Biology 27th annual conference. Shanghai, China Sep. 1-4, 2005.
Zelelew et al. "Application of digital image processing techniques for asphalt concrete mixture images" The 12th international conference of international association for computer methods and advanced geomachines (IACMAG). Goa, India, Oct. 1-6, 2008.
Zelelew et al. "A volumetric thresholding algorithm for processing asphalt concrete x-ray CT images". International journal of pavement engineering, vol. 12, Issue 6, 2011, 543-551 (Abstract).
Zhang et al. "A new edge detection method in image processing", IEEE Proc. of the International Symposium on Communications and Information Technology. (ISCIT2005), 1, 445-448, 2005 (Abstract).
Zhou et al. "Edge detection and linear feature extraction using 2D random field model", IEEE transactions on pattern analysis and machine intelligence, 11(1), 84-95(1989).
Ziou et al. "Edge detection techniques—an overview" International Journal of Pattern Recognition and Image Analysis,1998.

\* cited by examiner

Overall Structure of a Quaternion Neural Network

*Wavelet-Based Binary Pattern Feature Extraction Method*

Examples of Prostatic Cancerous Images after
Ensemble Empirical Mode Decomposition (EEMD)

*Architecture of the Two-Stage Multi-Classifier System for Biopsy Classification*

Architecture of the Two-Stage Exemplary System for Prostate Cancer Gleason Grading Integrated Assessment of Histopathology Images Logarithmic Color Model – Prostate Cancer Image

SYSTEMS AND METHODS FOR QUANTITATIVE ANALYSIS OF HISTOPATHOLOGY IMAGES USING MULTICLASSIFIER ENSEMBLE SCHEMES

BACKGROUND OF THE INVENTION

1. Field of the Invention

The invention generally relates to cancer detection and classification. The present disclosure includes quantitative analysis of and predictive modeling from digitized histopathology images. This disclosure includes methods that integrate multiple image description methods and classification methods into robust computer systems for accurate detection and classification or grading of cancerous tissue samples.

2. Description of the Relevant Art

The microscopic analysis of histopathology samples is widely used as a cancer diagnosis method. Histopathology is a labor-intensive process requiring the preparation of biopsy material including fixation, freezing, sectioning and staining followed by analysis and interpretation. Together these process steps have traditionally led to turnaround times of days rather than hours. Furthermore, tissue assessment is routinely performed by human visual evaluation of the structural deviation of cellular and sub-cellular components to diagnose the malignancy and aggressiveness of various types of cancer. These judgments may not be reproducible due factors including the pathologist's skill level, fatigue, and experience. Moreover, there may be variability in the interpretation and application of the grading criteria, particularly when grading or scoring complicated tissue samples. For example, in the case of prostate cancer diagnosis, it has been shown that intra-observer and inter-observer reproducibility of the Gleason grading system ranges from 60% to 90%. Additionally, comparisons between the assigned grade to a needle biopsy and the grade of the corresponding prostate gland reflect under-grading of the biopsy in 42% of cases and over-grading in 15% of cases.

Surgical oncologists require precise information about the findings on biopsy samples, including prognostic indicators such as tumor grade, score, localization, and extent. In recent years, standards for the accuracy of this information have been increasing, thus creating additional work required for clinicians. These issues create the need for a fast, automated, and reproducible classification system based on quantitative characterization of histopathology images. Such a system would likely result in significantly improved accuracy in cancer diagnosis.

The inherent complexity and non-homogeneity of histopathology images make quantitative analysis and classification a challenging task. Histopathology images vary widely but a share some common characteristics. A few colors, defined by an applied stain, are present in each tissue sample. These colors highlight specific tissue structures; particular edges, and a various of textures. Objects such as glands and nuclear structures may randomly appear in the image with varying sizes and shapes.

Due to the importance of imaging in cancer diagnosis and treatment and the advancement in digital pathology, computer-aided diagnosis has become an active research area in medical imaging and diagnostic radiology and pathology. The goal of histopathology-based computer-aided diagnosis is to increase the productivity of pathologists by improving the accuracy and consistency of diagnoses, reducing image reading time, and providing computer-based tools for image visualization and annotation.

Several systems for cancer detection and grading have been developed in the past several years. While most researchers have focused on the development of segmentation and feature extraction methods, the present disclosure includes robust classification using biopsy-image normalization methods in conjunction with multi-classifier ensembles. Most existing works compare the performance of various classifiers on a feature set and select the one that exhibits the best performance in terms of accuracy or computational complexity.

The present invention further provides improved classification methods and a novel method of creating multi-classifier ensembles. Most existing classification methods are based upon real numbers, and therefore process images in monochrome. When processing color image data, the standard technique is to process each color channel separately and to recombine the image after processing. However, using this method, correlations between color channels are lost. Since humans perceive thousands of colors but only ten to fifteen levels of grayscale, present classification methods do not necessarily provide optimal performance.

One potential solution is the use of quaternion numbers for the representation of image data. Since each quaternion value is in the four-dimensional Hamiltonian space, three- and four-dimensional color data naturally lends itself to representation with quaternions. Using quaternion signal processing, all color channels may be processed simultaneously, potentially providing improved processing results.

Real-valued neural networks and the associated back-propagation training algorithms, independently introduced as a multi-layer perceptron structure by a variety of researchers, have been used for classification in many applications. However, real-valued neural networks process images in monochrome, therefore leading to the aforementioned problems with recombining the color planes. Therefore, a quaternion neural network may improve classification performance when utilizing color images.

A major drawback to quaternion neural networks is their computational cost: The multiplication of two quaternions requires sixteen real multiplications, instead of one multiplication for real numbers. Therefore a high-speed training algorithm for quaternion neural networks is needed to render a quaternion neural network practical and one is disclosed herein.

Additional background art includes those systems proposed in the following patents or patent applications:

U.S. Pat. No. 7,761,240 B2, authored by Saidi et al., discloses systems and methods for automated diagnosis and grading of tissue images based on morphometric data extracted from the images by a computer in a 2-step procedure (detection and grading). These systems have not explored the integration among the color channels, which could improve the features extraction steps.

U.S. Pat. No. 8,139,831 B2, authored by Khamene et al., provides a method for unsupervised classification of histological images obtained from a slide simultaneously co-stained with NIR fluorescent and H&E stains. In this system, only gland centroids are used for graph construction. Some other important structures such as cell nuclei were not explored as a nodes of Voronoi, Delaunay and MST graphs. A significant drawback of this method is that additional an NIR stain must be used; the most widespread in clinical practice is H&E stain.

U.S. Pat. App No. 2010/0098306 A1, authored by Madabhushi et al., relates to computer-aided diagnosis using content-based retrieval of histopathological (prostate/breast/renal) image features based on predetermine criteria and their analysis for malignancy determination. The maximum reported accuracy is substantially worse than that obtained by the embodiments disclosed herein.

U.S. Pat. App No. 2011/0243417 A1, authored by Madabhushi et al., discloses a method and a system for detecting biologically relevant structures in a hierarchical fashion, beginning at a low-resolution. The relevant structures are classified using pairwise Markov models. The maximum reported accuracy is substantially worse than that obtained by the embodiments disclosed herein.

U.S. Pat. App No. 2007/0019854 A1, authored by Gholap et al., discloses a method and a system that provides automated screening of prostate needle biopsy specimen in a digital image of prostatectomy specimen. Among other differences, the segmentation methodology taught by Gholap differs significantly from the present disclosure.

U.S. Pat. App No 2010/0312072, authored by Breskin et al., discloses a method of estimating the grade of a prostate cancer sample using zinc data associated with the prostate. The assessment of cancer severity is not made from histological quantitative analysis of tissue images.

U.S. Pat. US 7,899,625 B2, authored by Bhanot et al., provides a classification method for cancer detection from mass spectrometry data. This system differs from the systems disclosed in the present invention in various aspects: the data patterns come from a different domain, therefore all pre-processing and feature extraction methods are different. In addition, the multi-classifier ensemble scheme does not contain grading classifiers as disclosed herein, and the attendant advantages, including a reduction in the complexity of combination algorithms.

U.S. Pat. App No US 20090297007 A1, authored by to Cosatto et al., discloses systems and methods for analyzing biopsy images based solely on nuclear information. A drawback of the system is that it is not able to grade or score a detected cancer region.

U.S. Pat. App No WO 2009006696 A1 authored by Louis Dagenais and Samantha Gallagher discloses systems and methods for processing for visualization and analysis of anatomical pathology images. More specifically, the Dagenais and Gallagher invention provides a method for digital pathology comprising the steps of: (i) obtaining at least one spectrally distinct digital images of the tissue sample; and (ii) preparing a tissue map from said at least one image in order to characterize tissue features and thereby classify tissue type and condition. Unfortunately, while this level of automation has improved the physical handling of pathology images, it has provided no concrete assistance to pathologists such that the accuracy of diagnosis needs to be improved [WO 2009006696 A1].

The systems and methods disclosed in the present invention offer several advantages in terms of accuracy and generalization ability over previously developed systems. The diversity of classifiers and the ensemble schemes described herein makes the systems suitable for application to different cancer recognition problems, without constrains related to color variations, scale, image magnification, feature vectors, and so on. In addition, the use of multi-classifier systems favors the use of specialized sub-systems based on a group of features or tissue descriptors. Moreover, the disclosed computer-aided diagnosis systems have been designed to process particular biopsy regions of interest or whole-slides of tissue samples from several body tissues. The methods and systems disclosed are completely general and independent of the process under consideration.

SUMMARY OF THE INVENTION

The present invention provides systems and methods for automated classification of cancerous lesions from digitized histopathology images using multi-classifier ensemble schemes. According to several aspects of the invention, robust multi-classifier systems are built based on the fusion or analysis of the predictions of base-level classifiers through one or more layers of meta-classifiers or refinement classifiers. Furthermore, the present disclosure introduces new methods for data representation and classification.

In one embodiment, the invention discloses new methods for modeling cancerous tissue of different grades using multi-resolution local binary patterns with a varying threshold. The modified local binary pattern operator is applied to the resulting wavelet transform coefficients.

In another embodiment, quaternion wavelet features are also integrated into a recognition system, in order to capture the tissue's structural information using the magnitudes and phases of hyper-complex wavelet coefficients.

The features extracted using the methods mentioned along with other color, texture, and morphology features are employed to train, test and calibrate data classifiers. The results of several machine learning tools trained on diverse pattern data are combined to produce a robust predictor that accurately detect various types and grades or scores of cancerous lesions. In one embodiment, a two-stage multi-classifier system is composed of a multi-class quaternion neural network and several refinement classifiers. The refinement classifiers reclassify an input pattern when two or more classes have similar posterior probability at the output of the base classifier (i.e. output quaternion neural network in the example above). Moreover, another embodiment of the disclosure provides a multi-classifier scheme wherein the prediction of several base-level classifiers are effectively combined by means of one or more layers of meta-classifiers and refinement classifiers.

Various aspects of the present disclosure relate to new structures and training algorithms for quaternion neural networks. The neural network of this disclosure is separated into a series of layers as shown in FIG. 1. Each layer consists of a vector or matrix multiplication followed by an activation function, which may be linear or non-linear. The layers of the neural network are interconnected, and structural connections may vary according to the classification problem to be solved. Several network connection structures may be used. For example, the neural network layers may be connected in a feed-forward structure, the interconnected layers may contain feedback paths containing multiple layers, the output of a single neural network layer may provide input to multiple neural network layers in a feed-back or feed-forward structure, a neural network layer's output may be routed directly to the same layer's input, etc.

One embodiment of the present invention introduces a variable-rate learning algorithm for quaternion neural networks. The learning rate is varied at each training cycle according to the maximum Mean Square Error (MSE) computed for any single training pattern over all of the neuron outputs, though other heuristics besides MSE may also be employed. This learning rate adjustment algorithm lowers the learning rate as the network comes closer to convergence, in order to avoid significant problems with misadjustment.

In accordance with an exemplary implementation of the present invention, a robust recognition system for cancer diagnosis (cancer detection and grading) from biopsy samples includes: pre-processing digitized biopsy images; randomization of the data set for cross-validation; tissue description through color, texture, graph, and morphology features; conducting robust feature selection; and the training of and adjusting of base-level classifiers, meta-classifiers, and refinement classifiers. For data classification, any suitable algorithms may be used for building diverse base-level classifiers and refinement classifiers, and different classification methods can be integrated into the system. The selection of a classifier should be done based on the performance of the each individual classifier on training and validation sets. The selection of the complete set of classifiers should be done based upon the combined classifier performance on training and validation sets. The outputs of an exemplary computer-aided diagnosis system for prostate cancer provide information about the disease severity and the location and extension of cancerous tissue. In particular, the output of the system may provide a Gleason grade, a localized map of Gleason grades, the percentage of each Gleason grade in each slide, a Gleason score identifying the dominant grade and secondary grade, and/or a Gleason score identifying multiple grades for the data sample.

In another exemplary system, methods for detection of skin cancer according to histopathological features are disclosed; The computer-aided diagnosis system comprises the general steps of pre-processing, feature extraction, classification, and validation. The output of the system provides information about the nature of the lesion by classifying input data into major types of skin cancers: melanoma (MM), basal cell carcinoma (BCC), and cutaneous squamous cell carcinoma (SCC).

The exemplary computer-aided diagnosis systems of the present disclosure are robust in terms of accuracy, sensitivity, specificity, positive predictive value, and negative predictive value; and may be used to achieve standardized and reproducible cancer classification outcomes.

These and other aspects of the present invention will become evident upon reference to the following detailed description.

BRIEF DESCRIPTION OF THE DRAWINGS

Advantages of the present invention will become apparent to those skilled in the art with the benefit of the following detailed description of embodiments and upon reference to the accompanying drawings in which.

Figure 1:
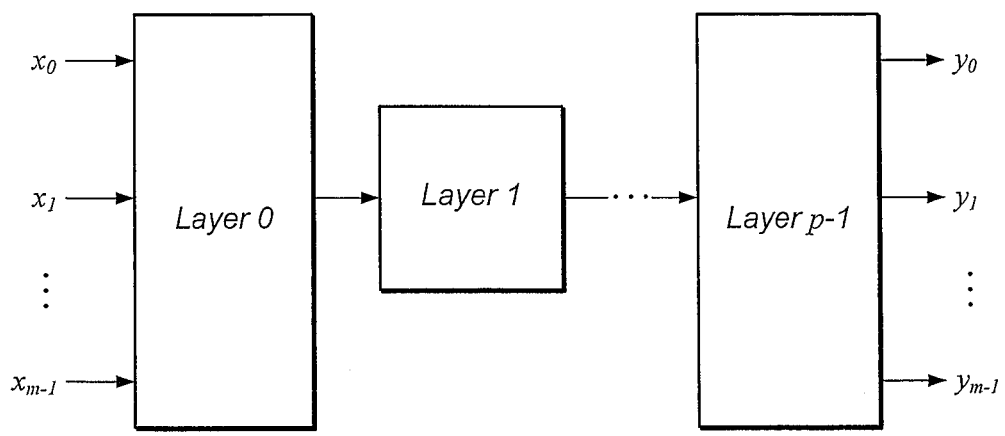
FIG. 1 is a functional block diagram showing an example of a structure of a quaternion neural network.

While the invention may be susceptible to various modifications and alternative forms, specific embodiments thereof are shown by way of example in the drawings and will herein be described in detail. The drawings may not be to scale. It should be understood, however, that the drawings and detailed description thereto are not intended to limit the invention to the particular form disclosed, but to the contrary, the intention is to cover all modifications, equivalents, and alternatives falling within the spirit and scope of the present invention as defined by the appended claims.

DETAILED DESCRIPTION OF THE PREFERRED EMBODIMENTS

It is to be understood the present invention is not limited to particular devices or methods, which may, of course, vary. It is also to be understood that the terminology used herein is for the purpose of describing particular embodiments only, and is not intended to be limiting. As used in this specification and the appended claims, the singular forms "a", "an", and "the" include singular and plural referents unless the content clearly dictates otherwise. Furthermore, the word "may" is used throughout this application in a permissive sense (i.e., having the potential to, being able to), not in a mandatory sense (i.e., must). The term "include," and derivations thereof, mean "including, but not limited to." The term "coupled" means directly or indirectly connected.

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

In this patent, certain U.S. patents, U.S. patent applications, and other materials (e.g., articles) have been incorporated by reference. The text of such U.S. patents, U.S. patent applications, and other materials is, however, only incorporated by reference to the extent that no conflict exists between such text and the other statements and drawings set forth herein. In the event of such conflict, then any such conflicting text in such incorporated by reference U.S. patents, U.S. patent applications, and other materials is specifically not incorporated by reference in this patent.

Further modifications and alternative embodiments of various aspects of the invention will be apparent to those skilled in the art in view of this description. Accordingly, this description is to be construed as illustrative only and is for the purpose of teaching those skilled in the art the general manner of carrying out the invention. It is to be understood that the forms of the invention shown and described herein are to be taken as examples of embodiments. Elements and materials may be substituted for those illustrated and described herein, parts and processes may be reversed, and certain features of the invention may be utilized independently, all as would be apparent to one skilled in the art after having the benefit of this description of the invention. Changes may be made in the elements described herein without departing from the spirit and scope of the invention as described in the following claims.

Disclosed herein are systems and methods for the automated classification of digitized histopathology images. Through the introduction of new features and a new classification technique, the disclosed systems further improve upon the performance of the systems disclosed by the Inventors in patent application WO 2013/049153 A2. The present invention provides methods for quantitative modeling and analysis of biopsy tissue samples for the diagnosis of several types of cancers, including cancer detection, grading, and scoring. This section describes new algorithms for mathematical description of biopsied tissue through textural and morphological features, and cancerous lesion classification using multi-classifier ensemble schemes. Moreover, a new algorithm for high-speed training of quaternion neural networks is disclosed and used for tissue classification in some embodiments of the invention. The disclosed systems' classification output may be used for creating localized cancer maps, measuring the extent of tumors, and, in the case of cancer scoring, determining the area occupied by each applicable cancer grade. Details are as follows.

One aspect of the present invention provide a variable rate learning algorithm for neural networks. Many algorithms in the field of machine learning require an iterative training process before use in applications such as prediction, system modeling, and so on. At each training cycle, input patterns are presented to the structure along with a desired response; the purpose of the iterative training process is to minimize the difference between the actual structure output and the desired response for each given pair of input pattern and desired response. The training process is thus an error minimization problem. Most training algorithms, such as the well-known backpropagation algorithm for neural networks, utilize the error signal generated by taking the difference of the desired response and the true network response to update parameters within the model. The size of the parameter update is typically controlled by a learning rate variable, traditionally named $\mu$.

The disclosed invention provides a means of varying the learning rate $\mu$ at each training cycle to reduce the number of required training cycles while avoiding the problem of misadjustment. Misadjustment error occurs when an iterative learning algorithm has nearly converged to the optimal solution, but cannot actually find the optimal solution due to a learning step size that is too large. Since the step size is too large, the algorithm continually overcorrects by adjusting the neural network or filter weights too much. In the case of a linear LMS filter, one can imagine using gradient descent on a parabolic surface to find the minimum of the surface. If the linearized weight updates are too large, the learning algorithm will find solutions on alternating sides of the minimum, but never the minimum itself. This is the problem of misadjustment, which is clearly worse with larger values of $\mu$. Neural network training algorithms exhibit similar behavior, but with non-convex performance surfaces. An exemplary implementation of the disclosed invention for use in the training of quaternion neural networks is described below.

During the training phase, a mean square error (MSE) value 1 for the network is computed at each training cycle k as follows:

$$\varepsilon^{(k)} = \max_p |\eta_p^{(k)}|_2 \qquad \text{Equation 4}$$

where $$\eta_p^{(k)} = \frac{1}{m} \cdot \sum_{0 \leq i < m} (d_{p,i} - y_{p,i}^{(k)})^2 \qquad \text{Equation 5}$$

p indexes the set of training patterns, i indexes the set of output neurons, m is the number of output neurons in the neural network, $d_{p,i}$ is the desired training response for pattern p at output neuron i, and $y_{p,i}^{(k)}$ is the neural network output for pattern p at output neuron i at training cycle k. The $\varepsilon^{(k)}$ MSE value corresponds to the maximum 2-norm of the MSE for any single training pattern over all of the neuron outputs. In Equation 4, $\eta_p^{(k)} \in \mathbb{H}$ and $\varepsilon^{(k)} \in \mathbb{R}$. The squaring operation in the computation $\eta_p^{(k)} \in \mathbb{H}$ is a dimension-wise squaring in $\mathbb{H}$ and does not denote quaternion multiplication. It should be noted that most neural network literature discusses the MSE for each neuron's output over all of the training patterns; the value for $\varepsilon^{(k)}$ computed above is different.

Equation 6 is used to adjust the learning rate $\mu^{(k)}$ at each training cycle k:

$$\mu^{(k)} = \begin{cases} \alpha \cdot \mu^{(k-1)} & \text{if } \varepsilon^{(k)} < \gamma \cdot \varepsilon^{(k-1)}, \\ \beta \cdot \mu^{(k-1)} & \text{otherwise} \end{cases} \qquad \text{Equation 6}$$

where $\alpha > 1.0 > \beta$ and $\gamma > 1.0$. This equation increases the value for $\mu$ if the maximum pattern MSE $\varepsilon$ does not grow too quickly, as defined by $\gamma$. Should the error grow too quickly, the value of $\mu$ is reduced by multiplication with $\beta < 1.0$. Should the value of $\mu^{(k)}$ be reduced as compared to $\mu^{(k-1)}$, the neural network weights from training cycle k−1 are also restored, as it is assumed that the most-recent weight update used too large of a learning rate. Typical values for $\alpha$, $\beta$, and $\gamma$ are 1.05, 0.70, and 1.02, respectively.

Figure 2:
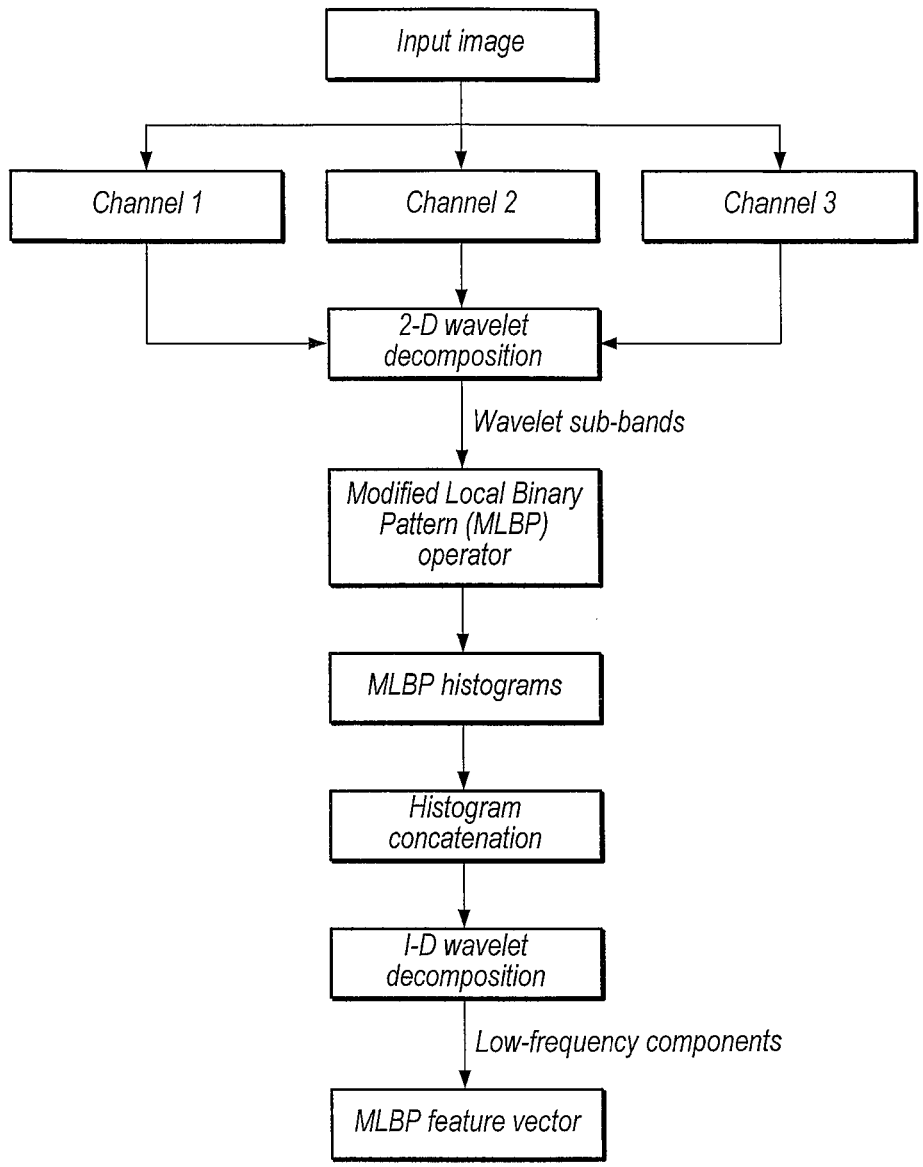
FIG. 2 is a functional block diagram of an example of wavelet-based binary pattern feature extraction method of the present invention.

In another aspect, the present invention provides a Wavelet-based local binary pattern features. A color-normalized image is decomposed into their three channels, namely red-green-blue (RGB). Each channel is processed independently according to the following procedure, which is also pictured in FIG. 2. First, 2-D wavelet decomposition is performed. The input image $I_0(x,y)=A_0(x,y)$ is represented by a set of orthogonal or orthonormal basis using scaling and translation operations on a mother wavelet function. Given wavelet analysis filters $\{h_n\}$ and $\{g_n\}$, the $k^{th}$ level wavelet decomposition is defined by:

$$A_k(x, y) = \sum_{m,n \in Z} h(m)h(n)A_{k-1}(2x - m, 2y - n), \qquad \text{Equation 7.1}$$

$$H_k(x, y) = \sum_{m,n \in Z} h(m)g(n)A_{k-1}(2x - m, 2y - n), \qquad \text{Equation 7.2}$$

$$V_k(x, y) = \sum_{m,n \in Z} g(m)h(n)A_{k-1}(2x - m, 2y - n), \qquad \text{Equation 7.3}$$

$$D_k(x, y) = \sum_{m,n \in Z} g(m)g(n)A_{k-1}(2x - m, 2y - n), \qquad \text{Equation 7.4}$$

which correspond to the 3k+1 wavelet sub-bands, wherein $A_k$ is a low resolution approximation of the original image and $H_{k,i}$, $V_{k,i}$, and $D_{k,i}$ are the detail coefficients representing horizontal, vertical and diagonal edge information at different scales i. Any wavelet analysis filters may be used. Examples of wavelet families include Daubechies, Coiflets, Discrete Meyer, Symlets, Bi-orthogonal, Fibonacci, Slant-Haar, and others. In particular, Haar wavelet is preferred since it is computationally efficient.

After the input image have been decomposed into a series of wavelet sub-bands, the modified local binary pattern MLBP codes of resulting sub-band are calculated by using the local binary pattern (LBP) operator with varying threshold. The LBP value for the center pixel $g_c$ located at the position (x,y) of a wavelet sub-band is calculated using the P pixels in a neighborhood of radio R at the $k^{th}$ decomposition level as $$MLBP_{P,R,k} = \sum_{p=0}^{P-1} s(g_p - g_c) 2^p \qquad \text{Equation 8}$$

The function s(x) is defined as a thresholding function s(x)=1 for x≥T and s(x)=0 otherwise. The described operation is performed for a set of discrete or continuous values of T∈[0,30]. The MLBP uniform patterns obtained using wavelet coefficients at each sub-band are represented by histograms, which are then concatenated. The concatenated signal is decomposed using a 1-D wavelet decomposition with any 1-D wavelet analysis filter, including the ones mentioned previously. Finally, the resulting approximation coefficients are used to build the MLBP feature vector. Since the quaternion neural network enables the use of hypercomplex feature vectors, the information from each image channel is assigned to a dimension of the quaternion input feature vector., In a further embodiment, the present invention provides a Wavelet features from a logarithmically modulated color space. A color-normalized image is logarithmically transformed to an invented color space based on the combination of logarithmic ratio of color space components, for example RGB (Red, Blue, and Green) space components:

$$R_r = R\left[\alpha_1 \log\left(\frac{R+1}{G+1}\right) + \beta_1 \log\left(\frac{R+1}{B+1}\right)\right] \qquad \text{Equation 9.1}$$

$$G_r = G\left[\alpha_2 \log\left(\frac{G+1}{R+1}\right) + \beta_2 \log\left(\frac{G+1}{B+1}\right)\right] \qquad \text{Equation 9.2}$$

$$B_r = B\left[\alpha_3 \log\left(\frac{B+1}{R+1}\right) + \beta_3 \log\left(\frac{B+1}{G+1}\right)\right] \qquad \text{Equation 9.3}$$

where $\alpha_i$ and $\beta_i$, i=1, 2, 3 are some constant, for example $\alpha_i = \beta_i = \frac{1}{2}$, i=1, 2, 3.

Each new channel is processed through wavelet decomposition using equations 7.1-7.4 in order to obtain approximation and detail coefficient matrices at k decomposition level $\{A_k(x,y), H_k(x,y), V_k(x,y), D_k(x,y)\}$. Any wavelet analysis filters may be used. Examples of wavelet families include Daubechies, Coiflets, Discrete Meyer, Symlets, Bi-orthogonal, Fibonacci, Slant-Haar, and others. In particular, Haar wavelet is preferred since it is computationally efficient.

In some embodiments the texture descriptor is composed by statistics (i.e. mean, standard deviation, and interquartile range) of the maximum absolute value of the channel wavelet coefficients at given position and scale, as follows:

$$A_{k,max}(x,y) = \max(|A_{k,R_r}(x,y)|, |A_{k,G_r}(x,y)|, |A_{k,B_r}(x,y)|) \qquad \text{Equation 10.1}$$

$$H_{k,max}(x,y) = \max(|H_{k,R_r}(x,y)|, |H_{k,G_r}(x,y)|, |H_{k,B_r}(x,y)|) \qquad \text{Equation 10.2}$$

$$V_{k,max}(x,y) = \max(|V_{k,R_r}(x,y)|, |V_{k,G_r}(x,y)|, |V_{k,B_r}(x,y)|) \qquad \text{Equation 10.3}$$

$$D_{k,max}(x,y) = \max(|D_{k,R_r}(x,y)|, |D_{k,G_r}(x,y)|, |D_{k,B_r}(x,y)|) \qquad \text{Equation 10.4}$$

In another embodiment, the present invention provides a method for extracting tissue features using visual morphology and local binary patterns. A color-standardized image is filtered using morphological filters with of with window structures of n×n pixels. The filter window may have any structure or shape. It may be a square, a line, a cross, etc. One common morphological operation filter used is the maximum/minimum filter. As an example, the result of the filter is computed pixel by pixel as follows:

$$\left(\frac{\max(p_i)}{\min(p_i)}\right)^\alpha \qquad \text{Equation 11.1}$$

$$\left(\frac{\log(\max(p_i))}{\log(\min(p_i))}\right)^\alpha \qquad \text{Equation 11.2}$$

$$\left(\frac{\log(\log(\max(p_i)))}{\log(\log(\min(p_i)))}\right)^\alpha \qquad \text{Equation 11.3}$$

$\alpha$ is a tuning parameter that can be used to enhance fine edges of the image and $p_i$ is the $i^{th}$ pixel of the filter window. Once the filtered image is obtained, it is decomposed using any wavelet filter as presented in equations 7.1-7.4. The approximation coefficients are encoded using the local binary pattern approach defined in equation 8, which give a compact and multi-resolution representation of the tissue image. The feature vector is formed by concatenating the histogram of the local binary patterns and the entropy of the local binary representation at each wavelet decomposition scale.

The Quaternion Wavelet Transform (QWT) is a hypercomplex extension of the real wavelet transform. The concept has been used previously for texture identification, but it has not been applied to prostate cancer grading. The QWT may be implemented using the dual-tree algorithm, which utilizes a real filter bank and their corresponding Hilbert pairs as a complex 1-D wavelet. These two filter banks lead to four separable filter banks that can be combined to fit the QWT definition. As in the case of real wavelet coefficients, the resulting QWT coefficients are separated into 4 sub-bands at each decomposition level, but they are quaternion numbers of the form $q = a + bi + cj + dk = |q|e^{i\varphi}e^{j\theta}e^{k\psi}$, whose magnitude is given by $$|q| + \sqrt{a^2 + b^2 + c^2 + d^2} \qquad \text{Equation 12}$$

and phases by $$\varphi = \frac{1}{2}\tan^{-1}\left(\frac{2(cd + ab)}{a^2 - b^2 + c^2 - d^2}\right), \qquad \text{Equation 13.1}$$

$$\theta = \frac{1}{2}\tan^{-1}\left(\frac{2(bd + ac)}{a^2 + b^2 - c^2 - d^2}\right), \qquad \text{Equation 13.2}$$

$$\text{and } \psi = \frac{1}{2}\sin^{-1}(2(ad - bc)). \qquad \text{Equation 13.3}$$

The QWT feature vector is composed by statistics of the coefficients' magnitude and phase along with the generalized energy of coefficients at each decomposition level. The energy is computed as $$E_{s,k} = \frac{1}{I_{0E}} \sum_{xy} |q_{xy}|^p \qquad \text{Equation 14}$$

where $E_{s,k}$ is the energy of the sub-band s=1,2,3,4 corresponding to approximation, horizontal, vertical, and diagonal sub-bands; and k=1,2 . . . K is the QWT decomposition level. $I_{OE}$ is a normalization term proportional to the energy of the original input image; and p>2 is a real tuning parameter.

In a further embodiment, the present invention provides a two-stage multi-classifier system for classification of carcinomas from digitized biopsy slides. A multi-classifier system is disclosed for the classification of biopsy images involving different classes. The system consists of a pre-processing unit, an image decomposition unit, an image feature extraction unit, and one or more classifiers.

Pre-processing unit is used for image normalization and segmentation. At this step, color normalization and standardization methods are used to reduce biopsy color variations.

The image decomposition unit uses various methods to perform image decomposition. For example, channel decomposition, bit plane decomposition, human visual system-based decomposition, empirical mode decomposition (EMD), and others may be employed for generating image segments or sequences. Some of the aforementioned methods for image decomposition require color images to be decomposed into their component channels.

Empirical mode decomposition (EMD) was proposed by Huang et al. with the aim of adaptively representing non-linear and non-stationary signals as sums of zero-mean amplitude- and frequency-modulated components. EMD is an adaptive time-frequency data analysis method, wherein the basis for data decomposition is obtained from the data subject under analysis. The algorithm decomposes a signal into a set of Intrinsic Mode Functions (IMF) using an iterative approach. The iterative method to compute the Empirical Mode Decomposition can be summarized as follows:

For a given 1-D or 2-D signal x perform the following steps:
  Initialize the residue $r_0$=x and the IMF index j=1
  Extract the jth IMF by using the sifting process explained hereinafter
  Compute the residue $r_j=r_{j-1}-IMF_j$
  Repeat steps 2 and 3 with j=j+1 until the number of extrema in $r_j$ is less than 2 or the desired decomposition level has been reached.

In order to extract the IMFs, a sifting process is performed. This process consists of the following steps:
  Identify local extrema (local maxima and local minima) in a given neighborhood.
  Generate lower and upper envelope by interpolating local maxima and local minima respectively.
  Average lower and upper envelope point by point.
  Subtract the average envelope from the residual iteratively until IMF's properties are satisfied:
    IMF is a zero-mean function
    All the maxima and all the minima of an IMF will correspondingly be positive and negative.
    It will be narrowband but not necessarily mono-component allowing the existence of both amplitude and frequency modulation (AM/FM).
  Perfect signal reconstruction after EMD decomposition is achieved by adding all the IMFs and the residue of the decomposition:

$$x = \sum_{j=1}^{N} IMF_j + r_N \qquad \text{Equation 15}$$

Figure 3:
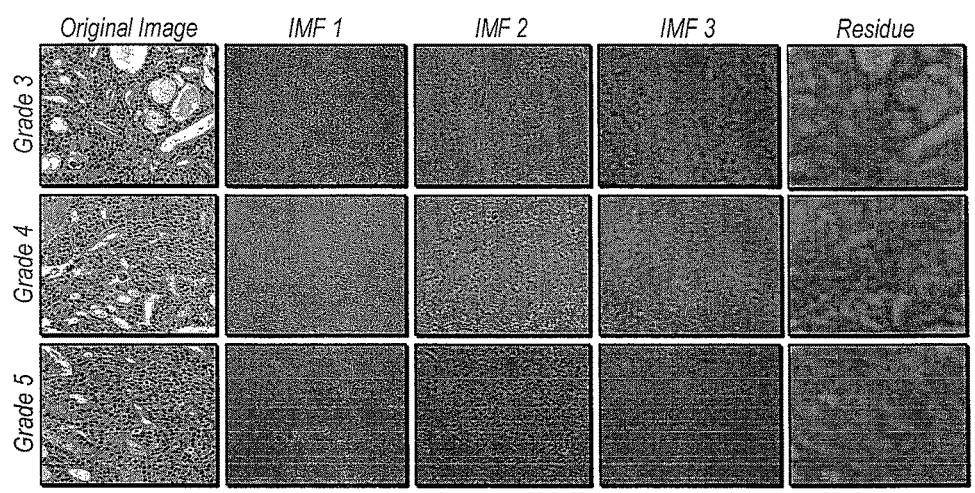
FIG. 3 is an examples illustrating of prostatic cancerous images after Ensemble Empirical Mode Decomposition (EEMD)

One problem that arises when a signal is decomposed using EMD is mode mixing. Mode mixing is defined as any IMF consisting of oscillations of dramatically disparate scales, often caused by intermittency of the driving mechanism. To solve the mode mixing problem, the Ensemble Empirical Mode Decomposition (EEMD) was proposed. The principle of the EEMD is to add several series of noise to the residual signal before performing the EMD decomposition. Once the noisy signals have been decomposed, the (ensemble) average of the corresponding IMFs and residues constitutes the final signal decomposition. Examples of images of prostatic carcinomas of Gleason 3, 4, 5 are shown after EEMD decomposition in FIG. 3.

Another method of performing image decomposition is the human visual system (HVS). HVS-based image decomposition methods have been used for image segmentation 49]}. HVS segmentation uses the background intensity and the rate of information change. The rate of information change X'(x,y) is calculated as a gradient measurement and derived using any edge-detection method. The background intensity at each pixel of the image is defined by:

$$B(x, y) = l \otimes \left[ l \otimes \left( \frac{l}{2} \otimes \sum_Q X(i, j) \oplus \frac{q}{2} \otimes \sum_{Q'} X(k, l) \right) \oplus X(x, y) \right] \qquad \text{Equation 16}$$

where X(x,y) is the input image, Q represents all of the pixels which are directly up, down, left, and right from the pixel located at (x,y) position, Q' represents all of the pixels diagonally one pixel away, l and q are predefined constant values.

In addition, a parameter $B_T$, which is the maximum difference in the input image, must be defined in order to determine the four regions of human vision response: least informative region (pixels below $x_1$), Devries-Rose region (from $x_1$ to $x_2$), Weber region (from $x_2$ to $x_3$), and saturation region (from $x_3$ to infinity).

$$B_T = \max(X(x,y)) \ominus \min(X(x,y)) \qquad \text{Equation 17}$$

The thresholds values $Bx_i$ defining each region can be computed as the multiplication of a parameter $a_i$ i=1, 2, and 3, and the threshold $B_T$. Next, these three regions are thresholded by the minimum gradient required for a human observer to notice a change Ki. The four image segments are defined as follows:

$$\begin{cases} Im_1 = X(x, y) & \text{if } Bx_2 \geq B(x, y) \geq Bx_1 \ \& \ \dfrac{X'(x, y)}{\sqrt{B(x, y)}} \geq K_2 \\ Im_2 = X(x, y) & \text{if } Bx_3 \geq B(x, y) \geq Bx_2 \ \& \ \dfrac{X'(x, y)}{\sqrt{B(x, y)}} \geq K_1 \\ Im_3 = X(x, y) & B(x, y) > Bx_3 \ \& \ \dfrac{X'(x, y)}{B(x, y)} \geq K_3 \\ Im_4 = X(x, y) & \text{All remaining pixels} \end{cases}$$

After image segmentation is complete, the feature extraction step is performed. Feature extraction performs computation of discriminant variables that describe the biopsy images in each region determined by the aforementioned image segmentation and decomposition steps. All the segments or a sub-group of segments are used for classification.

Textural methods in the spatial and transform domains as well as morphometric features may be used for image description.

Figure 4:
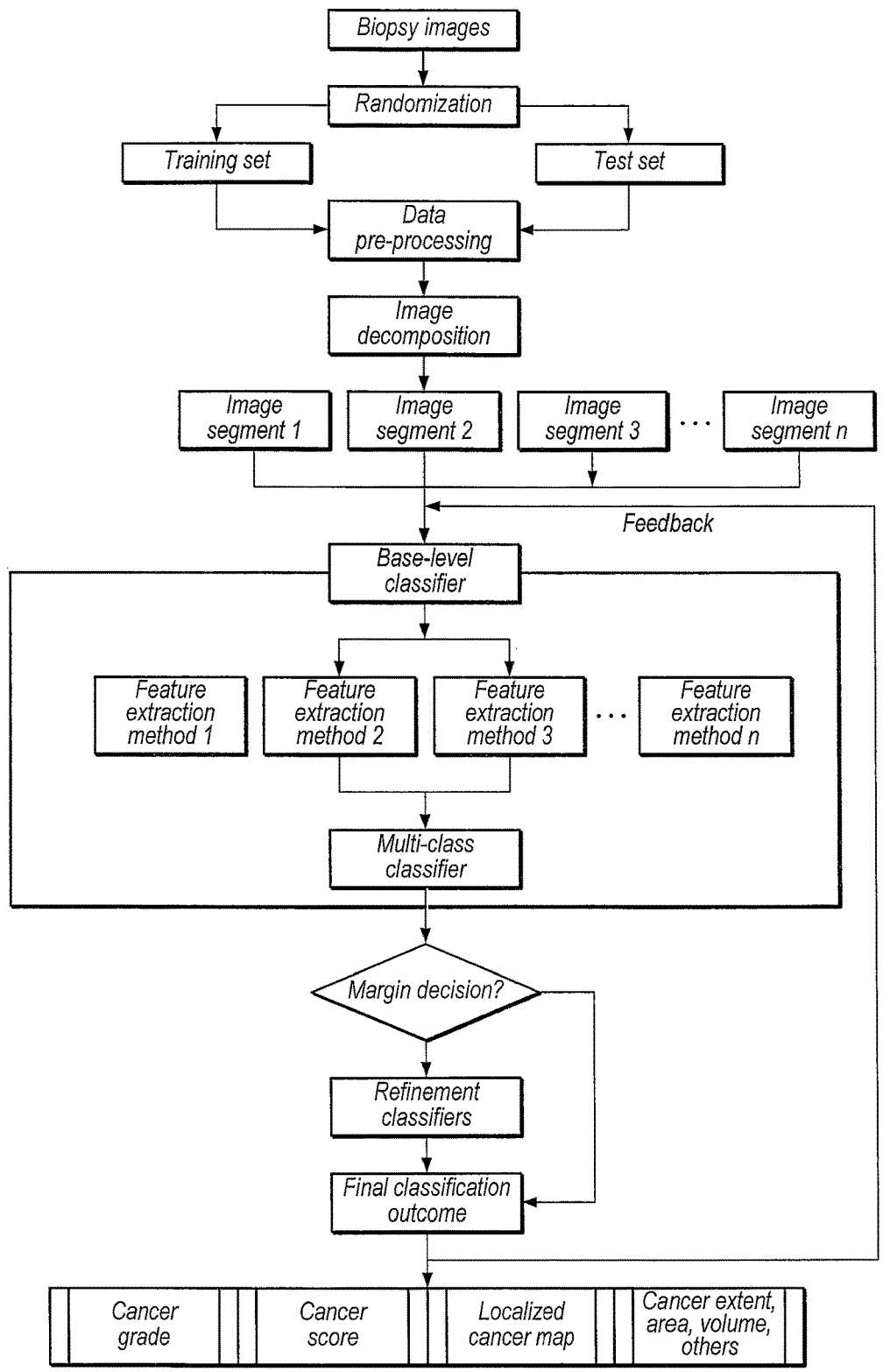
FIG. 4 is a functional block diagram showing an example of an architecture of the two-stage multi-classifier system for biopsy classification of the present invention.

Data classification in this embodiment is performed with the assistance of a two-stage classification system comprised of a multi-class classifier followed by refinement classifiers as shown in FIG. 4. The first stage might be composed by one or more classifiers depending on the multi-class classification approach. The second stage is composed by $$_MC_r = \frac{M!}{(M-r)! \cdot r!}$$

binary or multi-class classifiers used to correct or confirm the prediction of the base-level classifier. Each refinement classifier is trained on a small subset of r classes in order to learn more discriminative classification boundaries.

According to this embodiment, at least two different training subsets are required in order to build classification models for each system stage. The construction of training subsets from the available data can be achieved through several strategies. One of the most common approaches is to randomly divide the available data into disjoint subsets, ensuring that each resulting training group contains observations from all the classes. Another approach is to use different feature subsets, which leads to random subspace methods. Alternatively, different classifiers or classifiers parameters can be used to make diverse classifiers. The selection of an approach may be determined by the amount of available data and the number of discriminative features.

For data classification, any suitable algorithm can be used for building the base classifier and the refinement classifiers, and different classification methods can be integrated into the system. In an exemplary embodiment, the base-level classifier is a quaternion neural network classifier using the high-speed learning algorithm disclosed hereinbefore, and refinement classifiers are binary support vector machine classifiers. The selection of a classifier should be done based on the performance of the each individual classifier on training and validation sets. The selection of the complete set of classifiers should be done based upon the combined classifier performance on training and validation sets. It is important to point out that all classifiers should perform better than a random guess and that the estimated posterior probability for a predicted class at the output of refinement classifiers must be superior to the one of the base multi-class classifier.

Another aspect of this embodiment relates to a function, whose inputs are the class prediction of the base-level classifier and the a posteriori probabilities of each class. This process outputs a vector of two components that defines whether the second stage of the system is activated or not and which classifier is used to produce the final system outcome. The second-level classifiers reclassify an image using a different set of features only in the cases that two or more classes have similar a posteriori probabilities. The technique proposed in this embodiment presumes that class probabilities are available from the multi-class classifier. However, some classifiers such as SVM and K-NN do not output probabilities, but rather, values of the discriminant function, scores or distances. In such cases, a softmax function can be applied in order to convert those scores into approximated class probabilities. For example, in the case of SVM scores the following equation may be used:

$$P(c_m | x) = \frac{\exp(Sc_m)}{\sum_m \exp(Sc_m)} \quad \text{Equation 18}$$

In equation 18, m indexes the classes involved in the classification problem, and x is a d-dimensional vector representing the characteristics of an input pattern.

Similarly, the outputs of a K-NN classifier can be converted into a posteriori probabilities using several approaches. For example the posterior probability for class $C_m$ can be computed as:

$$P(c_m | x) = \frac{k_m}{K} \quad \text{Equation 19}$$

$k_m$ is the number of patterns among the K nearest neighbors (to point x) that belong to class $C_m$ and K is the number of neighbors used for classification.

Another alternative for the estimation of the K-NN classifier's posterior probability includes the distances from the input object x to the nearest neighbors as weighting factors. Let $Sc_m$ be the output score of the K-NN classifier for the class cm computed as:

$$Sc_m = \sum_i \frac{1}{d(x, k_{m,i})} \quad \text{Equation 20}$$

where $d(x, k_{mi})$ is the distance from the input vector x to all the patterns among the K nearest neighbors (to point x) that belong to class $C_m$.

Having the classifier score for each class, the softmax function of Equation 18 can be applied to obtain an estimation of the a posteriori probabilities of each class. Neural network classifiers, on the other hand, usually have a vector of desired responses that, if well trained, after softmax normalization may be used as posterior probability estimates.

Using the above or other transformations known to those skilled in probabilistic classification methods does not change the classification decision, but allows us to treat the classifier within a probabilistic framework.

Once the classifier predictions have been converted into posterior probabilities, they are ranked in ascendant order such that the r most probable classes and their respective posterior probabilities are used as input arguments of the function that selects the refinement classifier to be used in the second classification stage. The subscript (i) enclosed in parentheses indicates the $i^{th}$ most probable class; i can take integer values in the interval [1,r]. The first component of the output vector is a boolean variable calculated through a thresholding function that indicates whether or not any refinement classifier will be activated. The thresholding function is defined as follows:

$$S(P_{(1)}(c_k | x)) = \begin{cases} 1 & \text{if } P_{(1)}(c_k | x) \geq T \\ 0 & \text{if } P_{(1)}(c_k | x) < T \end{cases}, \quad \text{Equation 21}$$

The threshold is a real number in the interval (0, 1) and it can define according to the expected classification accuracy at the output of the base-level classifiers. The higher the threshold, the more test patterns are reprocessed by the refinement classifiers.

The second component of the output vector is the identification of the classifier that should be used for refinement. A look-up table can be queried passing over the m most probable classes as arguments upon which the ID of the refinement classifier to be used will be obtained. If the first component of the process output vector is 1, the test pattern is reclassified by the classifier given by the second component. Let $c_{m,1}$, $c_{m,2}$, and $c_{m,f}$ be the classes predicted by the base-level classifier, the refinement classifier and the whole system respectively; and $P(c_{m,1}|x)$, $P(c_{m,2}|x)$, and $P(c_{m,f}|x)$ their correspondent posterior probabilities. Then, the final outcome of the system will be defined by the following rules:

```
IF c_{m,1} = c_{m,2} THEN
    c_{m,f} = c_{m,1} = c_{m,2}
ELSE
    IF P(c_{m,1} | x) > P(c_{m,2} | x) THEN
        c_{m,f} = c_{m,1}
        P(c_{m,f} | x) = P(c_{m,1} | x)
    ELSE
        c_{m,f} = c_{m,2}
        P(c_{m,f} | x) = P(c_{m,2} | x)
    END_IF
END_IF
```

In order to estimate the performance of the classification methods or to adjust systems parameters, any cross-validation scheme (or other evaluation methods) can be used. In typical cross-validation, the training and validation sets must cross-over in successive rounds such that each data point has a chance of being validated against. Cross-validation is also useful to adjust system parameters by comparing the performance metrics obtained for different combination of such parameters. Performance indicators may include correct classification rate, sensitivity, specificity, positive predictive value, negative predictive value, and others. Correct classification rate is the ratio of correct classified cases to the total number of classified cases:

$$CCR = \frac{TP + TN}{totalSamples} \quad \text{Equation 22}$$

where TP and TN are true positive and true negative samples respectively.

Sensitivity is the proportion of cases belonging to a given class, which are correctly classified as cases of that class. That is, the sensitivity is the true positive rate (TPR)

$$TPR = \frac{TP}{TP + FN} \quad \text{Equation 23}$$

where FN represents the false negative samples.

Specificity is the proportion of non-cases of a specific class, which are correctly classified as non-cases of that class. That is, the specificity is the true negative rate (TNR)

$$TNR = \frac{TN}{TN + FP} \quad \text{Equation 24}$$

where FN represents the false positive samples.

Positive predictive value (PPV) is the proportion of those predicted to belong to a class, which really belong to that class $$PPV = \frac{TP}{TP + FP} \quad \text{Equation 25}$$

Negative predictive value (NPV) is the proportion of those predicted to be non-cases of a given class, which really do not belong to that class $$NPV = \frac{TN}{TN + FN} \quad \text{Equation 26}$$

EXAMPLE 1

Gleason Grading

Figure 5:
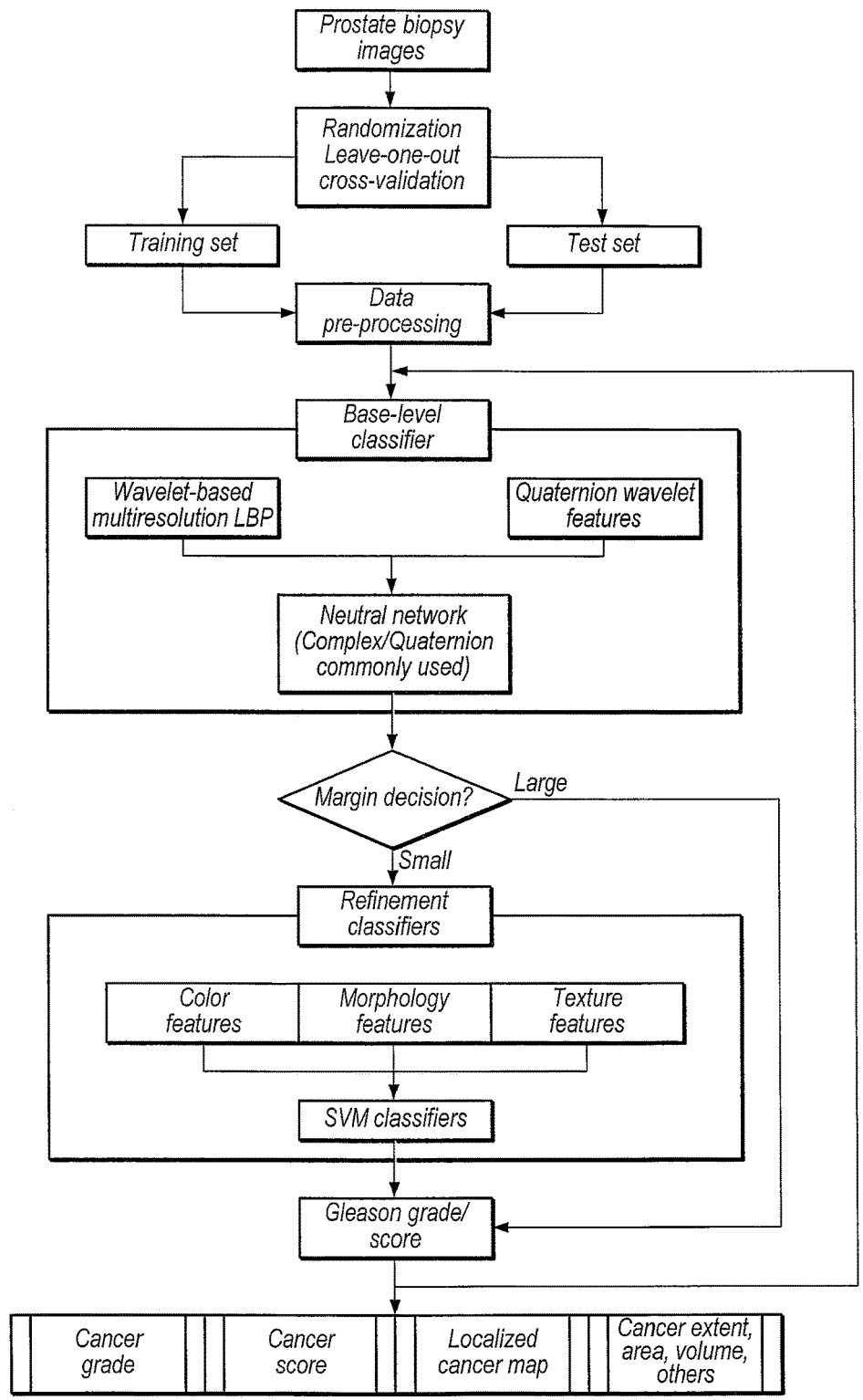
FIG. 5 is a functional block diagram showing an example of an architecture of a two-stage exemplary system for prostate cancer Gleason grading.

In this example a prostate cancer Gleason grading system was used to estimate the prostate cancer grade. Described herein is the framework for the development of a prostate cancer grading system. For purposes of the illustration of this embodiment of the present invention an example of a system for the grading of prostatic carcinoma from digitized histopathology slides is explained in detail. However, it must be understood that the present invention is also applicable to biopsies of other body organs including but not constrained to the skin, liver, breast, brain, kidney, pancreas, lungs, colon, rectum, bladder, cervix, and uterus. The input data may be small images of pre-selected regions of interest or whole-slides. When processing whole-slides, a grid of size s×s is placed over the image, and the classification process described below is performed once per resulting block. The general architecture of the system is illustrated in FIG. 5.

The description of processes carried out in the system will be set forth below according to the following outline. Note that steps 1 to 6 correspond to system operation in training mode and step 7 corresponds to system operation in classification mode.

[01] Construction of training data sets
[02] Randomization for cross-validation
    i. k-fold
    ii. Hold-out
    iii. Leave-one-out
[03] Image pre-processing
    i. Color normalization
    ii. Image segmentation
[04] Feature extraction
    i. Methods used on training set 1:
        1. Modified multi-resolution local binary pattern MLBP
        2. Quaternion wavelet transform features
    ii. Methods used on training set 2:
        1. 2-D color histograms
        2. Morphometric characteristics of tissue structures
        3. Color fractal dimension
        4. Real wavelet—based features
        5. Other textural models
[05] Building classification models
    i. Quaternion neural network (Multi-class base-level classifier)
    ii. Support vector machine (Refinement classifiers)

iii. Classifiers interaction process
[06] Validation and calibration
    i. Adjustment of system parameters based on cross-validation results
        1. Quaternion neural network parameters
        2. SVM kernel parameters
        3. Definition of posterior probability threshold
[07] Classification of new patterns
    i. Base-level multi-class classification
        1. Extraction of Quaternion wavelet transform and MLBP features
        2. Class prediction with Quaternion Neural Network classifier
    ii. Analysis of neural network classification margin
    iii. Re-classification (if needed) according to the output of the interaction process
        1. Pre-processing: Color normalization, image segmentation
        2. Extraction of color, textural, and morphology features
        3. Class prediction with Support Vector Machine refinement classifier The developed system uses the concept of supervised machine learning; therefore, the training patterns must be previously labeled to be used as a ground truth. In order to train the base-level classifier and the refinement classifiers, at least two representative training sets are built from digitized histopathology images that have been previously graded by expert pathologists. The approach used in this example for constructing diverse classifiers is to extract different features from the available data and use the extracted features when training classifiers at each stage of the system.

Randomization is performed for system validation. During validation, the available data is divided into complementary subsets: the analysis is performed on the training subset, and validation on validation or testing set. K-fold, hold-out or leave-one-out schemes can be used for partitioning the data.

Once the data is divided into training and testing sets, each pattern is subject to image pre-processing and feature extraction. Pre-processing methods include image normalization, scaling, tissue structures segmentation, and other operations directed to prepare the image for feature extraction. For example, image color normalization can be performed using the local color transference algorithm based on fuzzy image clustering presented in a previous embodiment, or any other method designed to achieve that goal.

After image pre-processing is performed, several methods can be used for tissue description. In general, feature vectors for histopathology images are based on texture, morphology, color, and graph features. In this example, textural features obtained with a modified local binary pattern operator and quaternion wavelet transform coefficients are employed to train the base-level quaternion neural network, while color, morphology, fractal, wavelet-domain features are used for refinement classifiers.

Referring now to the computation of the feature vectors, the multi-class classifier, which is a quaternion neural network in this example, is trained using features generated from wavelet-based local binary patterns and the quaternion wavelet transform.

Additional embodiments include other features that capture texture, geometry, morphometric and color information from biopsy images. Examples of those features include, but are not limited to, energy and entropy of wavelet detail coefficients, energy distribution of wavelet approximation coefficients, statistics of wavelet coefficients of image channels, fractal dimension, color histograms and entropy of dominant colors histogram, statistics of tissue structures area, perimeter, circularity, elliptic fit and ratio of average to maximum area and perimeter, nuclear density, and features from Delaunay triangulation, Voronoi graph and Minimum Spanning Tree graph.

According to an embodiment of the present invention, cancer classification from histopathology images is performed with the assistance of the two-stage multi-classifier system described hereinbefore, which is composed for illustration purposes by a quaternion neural network and various pairwise SVM classifiers. Cross-validation is employed for parameter selection, tuning and calibration of individual classifiers and for evaluation of system performance. In order to reduce the variability of performance indicators such as correct classification rate, sensitivity, and specificity, multiple rounds of cross-validation are performed using different partitions, and the validation results are averaged over the rounds.

Various simulations in accordance with this embodiment of the present invention were run on a database of 71 color images of Hematoxylin and Eosin (H&E)-stained prostate tissue samples. The dataset contains 30 image regions of Gleason 3, 30 of Gleason 4, and 11 of Gleason grade 5. Leave-one-out cross-validation was used to estimate the performance of the system. The average correct classification rate (CCR) and other indicators of system performance including sensitivity, specificity, positive predictive value (PPV) and negative predictive value (NPV) are summarized in Table 1.

TABLE 1

Performance indicators of the proposed 2-stage classification system averaged over 10 simulation runs.

|  | Grade 3 | Grade 4 | Grade 5 |
| --- | --- | --- | --- |
| CCR |  | 0.9831 |  |
| Sensitivity | 0.993 | 1.000 | 0.909 |
| Specificity | 1.000 | 0.971 | 1.000 |
| PPV | 1.007 | 0.962 | 1.102 |
| NPV | 0.995 | 1.030 | 0.983 |

The two-stage multi-classifier system achieves a remarkable accuracy of 98.31%, outperforming the existing systems for prostate cancer grading. The other indicators, namely sensitivity, specificity, PPV and NPV are also close to the ideal case of 1.000. Therefore, the experimental results demonstrate the ability of the proposed scheme to help pathologists in the diagnosis of prostate cancer more efficiently and with better reproducibility.

Figure 6:
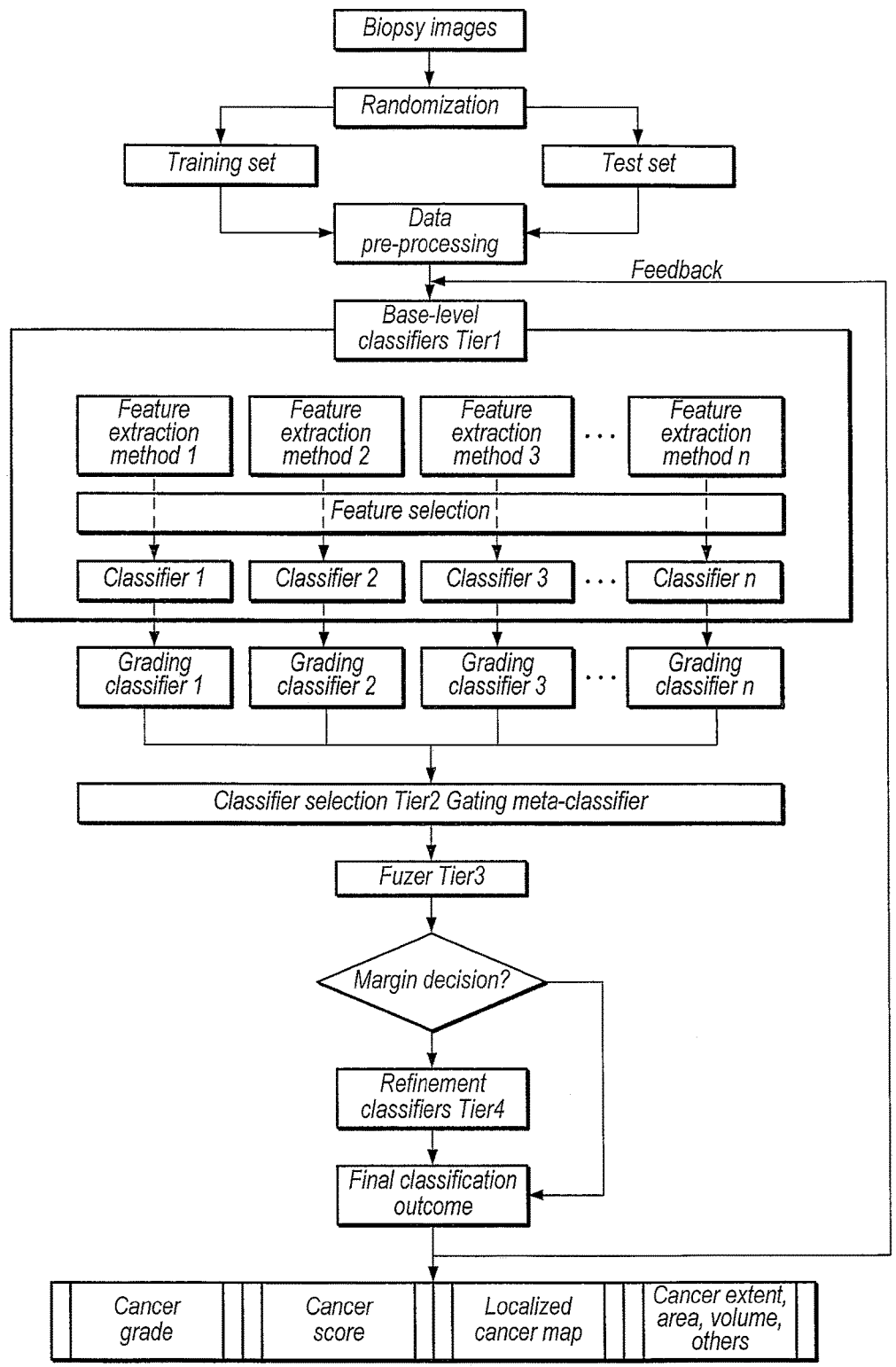
FIG. 6 is a functional block diagram showing an example of a multi-classifier ensemble using grading classifiers and fusion unit.

In a further embodiment, the present invention provides a system and methods for robust classification of biopsy images using multi-modal expert classifiers and meta-classification. Exemplary embodiments are described for prostate cancer Gleason grading and skin cancer classification. The system comprises image color normalization and tissue structure segmentation as a pre-processing steps, feature extraction, data classification and system validation as illustrated in FIG. 6. In the proposed system, various based-level expert classifiers are trained to recognize cancer grades or cancer types using independent feature domains. For instance, one classifier might be trained using modified local binary patterns (MLBP), a second classifier on Haralick features, another classifier on statistics of shape and size of tissue structures, and so on. In addition, different classification methods such as k-nearest neighbor (K-NN), logistic regression, ridge regression, support vector machine (SVM), artificial neural networks, decision trees, Bayesian classifiers, etc. may be integrated into the system. Using the mentioned approaches, diverse base-level classifiers may be constructed. However, other strategies might be used to ensure classifier diversity. With the assistance of grading meta-classifiers (one per base-level classifier), the proposed system is able to predict for each of the original base-level learning methods whether its prediction for a particular training example is correct or not. Only the predictions of base-level classifiers which are more likely to be right will be fused at the next stage. The predictions fusion may be performed by a non-trainable or trainable combiner that utilizes the predictions of selected based level classifiers to produce the final system output.

In accordance with an embodiment of the invention, the aforementioned multi-classifier ensemble is trained according to the following procedure: (1) n Tier-1 classifiers are trained and validated, based on a cross-validation partition of the available training data, which correspond to feature vectors computed using a different method per classifier; (2) m Tier-2 grading classifiers are trained, one or more for each base-level classifier. The input feature vector to each grading classifier consists of the original features with new class labels that encode whether the prediction of the corresponding base-level classifier was correct when classifying a particular training example; and, (3) a unit for classification fusion is used to make a decision based on the prediction of the base-level classifiers that are expected to be correct. This unit might use various combination approaches. For example, majority voting, weighted majority voting, Borda count, weighted average, trimmed mean, maximum, minimum, sum or product rules, template-based classification, meta-classification, and others may be employed to produce a preliminary or final classification decision. In an alternative embodiment of the invention, refinement classifiers may be used when, at the output of the fusion unit, two or more classes have similar a posteriori probabilities according to the rule stated in a previous embodiment.

Once the multi-classifier system has been trained, the automatic tissue classification processing may be performed. Digitized histopathology images are input into the pre-processing unit in order to normalize the color, scale, and segment tissue structures. Furthermore, in the case of whole-slide processing, a grid is established over the whole-slide image. Any suitable image analysis technique or combination of techniques may be used to perform image segmentation and color normalization, including the image analysis technique described herein based on fuzzy local color transference. After image pre-processing, the same feature extraction methods used in classifiers training are used. The generated features are then subject to classification, resulting in a biopsy diagnosis for cancer presence, classification, grade, or score.

It is important to point out that this embodiment assumes that posterior probabilities are available. If they are not, the equations 16, 17, and 18 may be used to compute an estimation of those probabilities.

EXAMPLE 2

Prostate Cancer

In this example a multi-classifier system was used to grade prostate cancer. Described herein is a system for grading and scoring of prostate cancer based on the Gleason grading system, which is presented as an exemplary application of the multi-classifier system for biopsy classification. The system is composed of a pre-processing unit and six base-level sub-systems. Each base-level sub-system is comprised of a feature extraction unit, a classification method, and, as necessary, a function to obtain posterior probabilities from the classification output. In addition, the multi-classifier system has a fusion unit and several binary classifiers for refinement tasks. The decision of the classifier ensemble is produced by using a dynamic weighted voting technique, which will be explained later in this section. The purpose of the binary refinement classifiers is to improve overall system accuracy.

Figure 7:
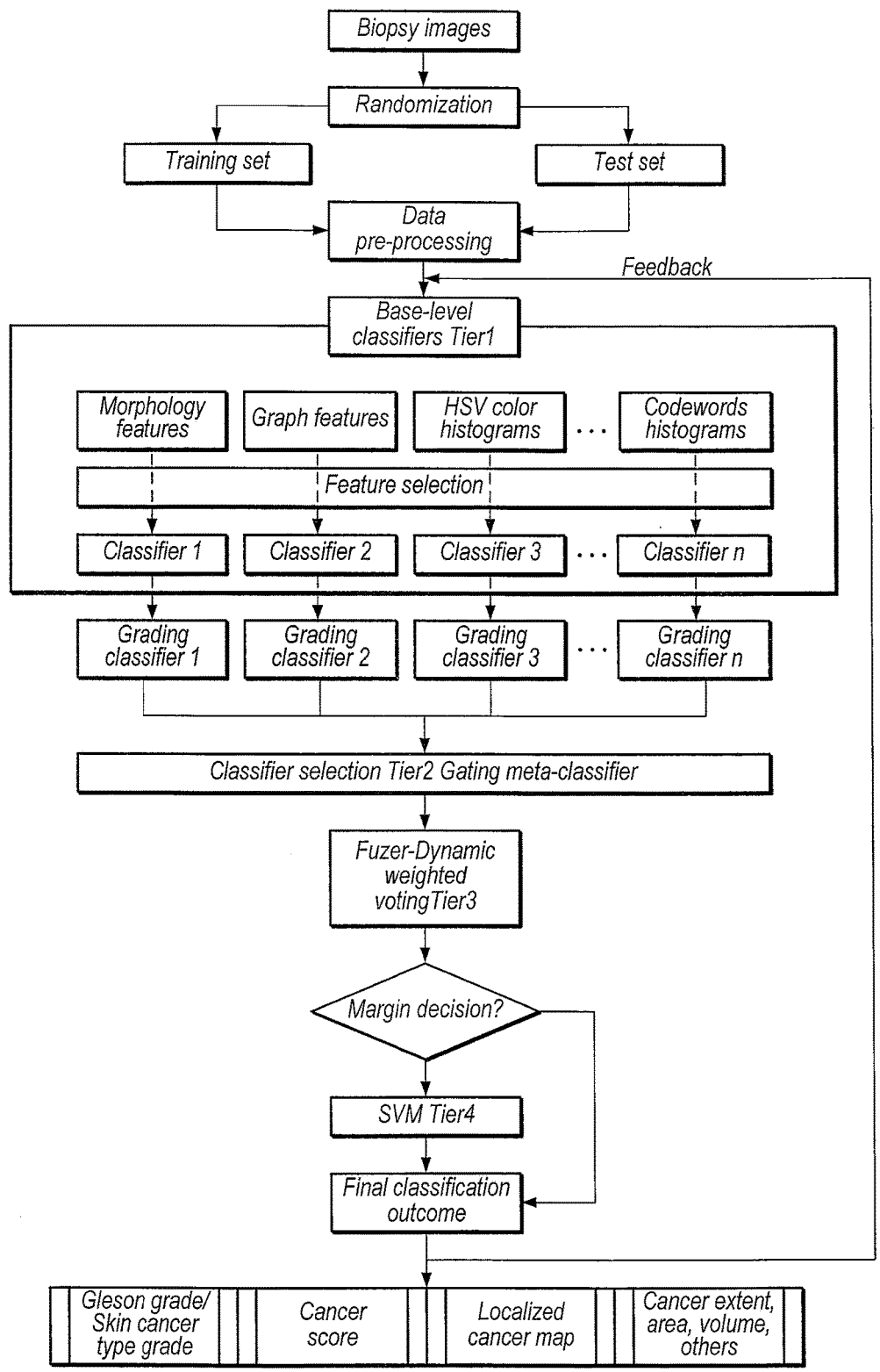
FIG. 7 is a functional block diagram showing an example of a multi-classifier system using multi-modal tissue descriptors for prostate and skin cancer classification.

The description of processes carried out in the system will be set forth below according to the FIG. 7 and the following outline. Note that steps 1 to 6 correspond to system operation in training mode and step 7 corresponds to system operation in classification mode.

[01] Construction of training data sets
[02] Randomization for cross-validation
  i. k-fold
  ii. Hold-out
  iii. Leave-one-out
[03] Image pre-processing
  i. Color normalization
  ii. Image segmentation
[04] Base-level classifiers training and validation
  i. Classifier 1: Morphology-based features
  ii. Classifier 2: Graph-based features
  iii. Classifier 3: Haar wavelet transform features
  iv. Classifier 4: HSV 2-D color histograms
  v. Classifier 5: Modified local binary pattern MLBP
  vi. Classifier 6: Codewords histogram
[05] Grading classifiers training
  i. Feature vector construction
  ii. Base-level classifiers' graded predictions as class label
[06] Validation and calibration
  i. Adjustment of system parameters based on cross-validation results
    1. Adjustments of parameters of grading classifiers
    2. Definition of posterior probability threshold for classification refinement
[07] Classification of new patterns
  i. Base-level multi-class classification
    1. Extraction of feature vectors: Morphology-based features, graph-based features, Haar wavelet transform features, HSV 2-D color histograms, and MLBP features.
    2. Classification using previously trained classifiers
  ii. Analysis of classifier ensemble classification margin
  iii. Re-classification (if needed) according to the output of the interaction process
    1. Pre-processing: Color normalization, image segmentation
    2. Extraction of color, textural, and morphology features
    3. Class prediction with Support Vector Machine refinement classifier In order to train the multi-classifier system, the available images of biopsy samples are first divided into two sub-sets using any suitable cross-validation approach. The training sub-set is further divided using the same or another cross-validation approach for training and validation of individual base-level classifiers. All images are subject to normalization and segmentation prior to feature extraction. In this example, color normalization is performed by using fuzzy local color transference disclosed hereinbefore. However, other algorithms such as color deconvolution, the Reinhard method, histogram matching, and non-linear color mapping might be used. Segmentation of tissue structures, including lumen, nuclei, cytoplasm, stroma, or entire gland units, may be performed using color-based approaches as disclosed by the Inventors in patent application WO 2013/049153 A2, thresholding, active contours or deformable models, or other methods.

For the exemplary system, five expert systems are trained based multi-modality feature vectors, which are computed as follows:

Morphology-based features: Once the tissue structures have been segmented using any set of suitable algorithms, including the ones discussed previously, size and shape features are calculated. The features include but are not constrained to statistics of lumen area, perimeter, circularity, elliptic fit (major axis length, minor axis length, orientation, and eccentricity), ratio of average to maximum of lumen area and lumen perimeter; statistics of glandular area, perimeter, circularity or roundness, spatial density of gland distribution, gland area covered by blue mucin, statistics of the distances from the lumen center to the nuclei boundary (gland radius), circularity, glandular elliptic fit, nucleus density, cancerous nucleus density, percentage of nucleus area in glandular area, nuclear area and circularity.

Graph-based features: Various graphs based on tissue structures centroids may be constructed. In particular, nuclear centroids can be used as graph nodes. Examples of features obtained from Voronoi tessellation and Delaunay triangulation include number of nodes, number of edges, cyclomatic number, number of triangles, number of k-walks, spectral radius, eigenexponent, Randic index, roundness factor, area, area disorder, roundness factor homogeneity, and network cycle features (non-triangular cycles, average network cycle length, maximum network cycle length). In addition, minimum spanning tree features may include number of nodes, edge length, degree, number of neighbors, Wiener index, eccentricity, Randic index, Balaban index, fractal dimension, and network cycle features.

Wavelet transform features: An input image is decomposed using suitable wavelet analysis filters at a specific decomposition level. For example, the Haar wavelet transform may be used. In general, the color channels of the image are processed independently; however, inter-channel dependencies are also considered in this system. Examples of real wavelet features include energy and entropy of wavelet detail coefficients, statistics of wavelet coefficients (mean, variance, standard deviation, and higher-order statistical moments), the joint probability of wavelet coefficients obtained for each image channel, and low resolution images.

HSV 2-D color histograms: First, a color model transformation is performed on the input images. RGB are mapped into HSV (Hue, Saturation, and Intensity) channels. 2-D histograms are computed with HS, HV and SV channels. The number of bins of the histogram can be adjusted by cross-validation. 2-D histograms allow quantifying the presence and dispersion of colors in biopsy images.

Modified local binary pattern MLBP: The low-frequency components of uniform local binary patterns obtaining using wavelet-based multi-resolution analysis are used to construct a feature vector representing the overall trend of a 1-D signal containing local textural features at a several wavelet decomposition levels. The method and procedures for describing tissue using the wavelet-based MLBP is pictured in FIG. 2.

Codeword histogram: In order to construct a dictionary of codewords, independent features representing a given Gleason grade are constructed from small patches. First, a regular grid is placed on histopathology images containing fairly homogeneous Gleason grades and the blocks that best represent the image grade are stored as codeword candidates. Each block is subject to feature extraction for description. Textural features in spatial and wavelet domain and fractal-like features can be used to represent blocks; the most discriminative sets of computed features become members of the codeword dictionary. Preferably, the extracted features are locally invariant to rotation, translation, scaling, and other image parameters. Next, a histogram containing the rate of recurrence of each codeword within an image is constructed by matching blocks using a correlation or any other distance measurement. The resulting histogram is the feature vector, which is the input to a learning algorithm for image classification. Furthermore, the computed histogram is used to quantify the area occupied by each Gleason grade in a histopathology image corresponding to a region of interest or a biopsy whole-slide. A Gleason score with the two or three most frequent Gleason patterns is an output of the system if the most frequent pattern(s) in the histogram match the most probable classes according to the prediction of the multi-classifier system.

Note that the system does not have any restriction regarding the number of expert systems and the features used for tissue description and classification. Also, any classification method can be used for multi-class classification at the first stage of the system, or various classification methods can be integrated. The validation portion of data can be used to adjust the classifier parameters and improve the classification performance.

The method continues with the training of grading classifiers. A grading classifier is trained for each base-level classifier. The objective of each classifier is to learn if a base-level classifier will correctly classify a particular input image. The grading classifiers are binary classifiers, whose input feature vectors correspond exactly with the one of their respective base-level classifier and the possible classes are correct and incorrect. Classes can be represented by 1 and −1 respectively. Again, any classification algorithm may be applied to this two-class problem. In the case that no classifier is considered to be correct by the grading classifiers, the final decision is made including the predictions of all base learners.

The next step is the fusion of selected base-level predictions. Fusion can be performed by using non-trainable or trainable classifiers. In this example, a non-trainable approach called dynamic weighted majority voting is employed for prediction fusion. Each expert classifier makes a prediction and the weight of the prediction is defined by the number of correct classified k-nearest neighbors. To make an overall prediction, the fusion unit evaluates the weighted vote of the expert predictions, and predicts the class with the highest weight. The system produces an approximated a posteriori probability that will be used to determine whether or not refinement classifiers reprocess the input image.

Once the system is trained and ready for classification tasks, a previously unseen image is subject to normalization and segmentation using proper algorithms, including the ones used for training images. The described feature extraction methods are then applied to the images. Following this, each base classifier produces an initial class prediction, which are input to the fusion unit if the corresponding grading classifier predicts that the base classifier prediction is correct. The fusion unit uses the weighted voting strategy described above to define the output of the ensemble. If two or more classes have similar posterior probabilities, a refinement classifier will re-classify the image.

Various simulations in accordance with this embodiment of the invention were run on a database of color images of Hematoxylin and Eosin (H&E)-stained prostate tissue samples. The dataset contains 30 image regions of Gleason 3, 30 of Gleason grade 4, and 11 of Gleason grade 5. Leave-one-out cross-validation was used to estimate the performance of the system. For example, the average CCR, sensitivity, specificity, PPV, and NPV are summarized in Table 2.

TABLE 2

Performance indicators of the proposed system in prostate cancer grading averaged over 10 simulation runs.

|  | Grade 3 | Grade 4 | Grade 5 |
|---|---|---|---|
| CCR |  | 0.9622 |  |
| Sensitivity | 0.9500 | 0.9600 | 0.9200 |
| Specificity | 0.9600 | 0.9800 | 0.9750 |
| PPV | 0.9579 | 0.9792 | 0.9728 |
| NPV | 0.9833 | 0.9867 | 0.9733 |

The classification performance using the proposed multi-classifier ensemble succeeded in classifying clinically-significant prostatic Gleason patterns. The system is able to recognize Gleason grades 3, 4, and 5 with an average accuracy of 96.22%. Furthermore, the system is robust in terms of sensitivity and specificity, whose averaged values across all considered classes are close to the best-case value of 1.0000.

EXAMPLE 3

Skin Cancer Classification

In this example a Multi-classifier system was used to detect skin cancer. In order to demonstrate the general applicability of the disclosed system, the multi-classifier system of the previous example is also applied to the problem of skin cancer classification. The output of the system provides information about the nature of the lesion by classifying input data into major types of skin cancers: melanoma (MM), basal cell carcinoma (BCC), and cutaneous squamous cell carcinoma (SCC). Experiments were carried out on a database of 60 color images of Hematoxylin and Eosin (H&E)-stained skin tissue samples. The dataset contains 30 images of melanoma, 20 images of BCC, and 10 of SCC. Leave-one-out cross-validation was used to estimate the performance of the system. The average CCR, sensitivity, specificity, PPV, and NPV are summarized in Table 3.

TABLE 3

Performance indicators of the proposed system in skin cancer classification averaged over 10 simulation runs.

|  | Melanoma | BCC | SCC |
|---|---|---|---|
| CCR |  | 0.8667 |  |
| Sensitivity | 0.7800 | 0.8600 | 0.7600 |
| Specificity | 0.8300 | 0.9000 | 0.9700 |
| PPV | 0.7655 | 0.8667 | 0.9545 |
| NPV | 0.9074 | 0.9467 | 0.9183 |

EXAMPLE 4

In this example a Multi-classifier System was used to score Prostate Cancer. Prostate cancer score is the addition of the two predominant grades in a biopsy tissue core. In order to use the multi-classifier system disclosed in this invention, a grid is superimposed to the whole-slide images, such that the classification method is applied to each patch independently. Therefore, the individual grade and area of each patch is calculated and the score is computed by using the most probable distribution of grades within the slide. The area occupied by each tumor grade can be also estimated using the counts of pixels and the resolution of the image.

Figure 8:
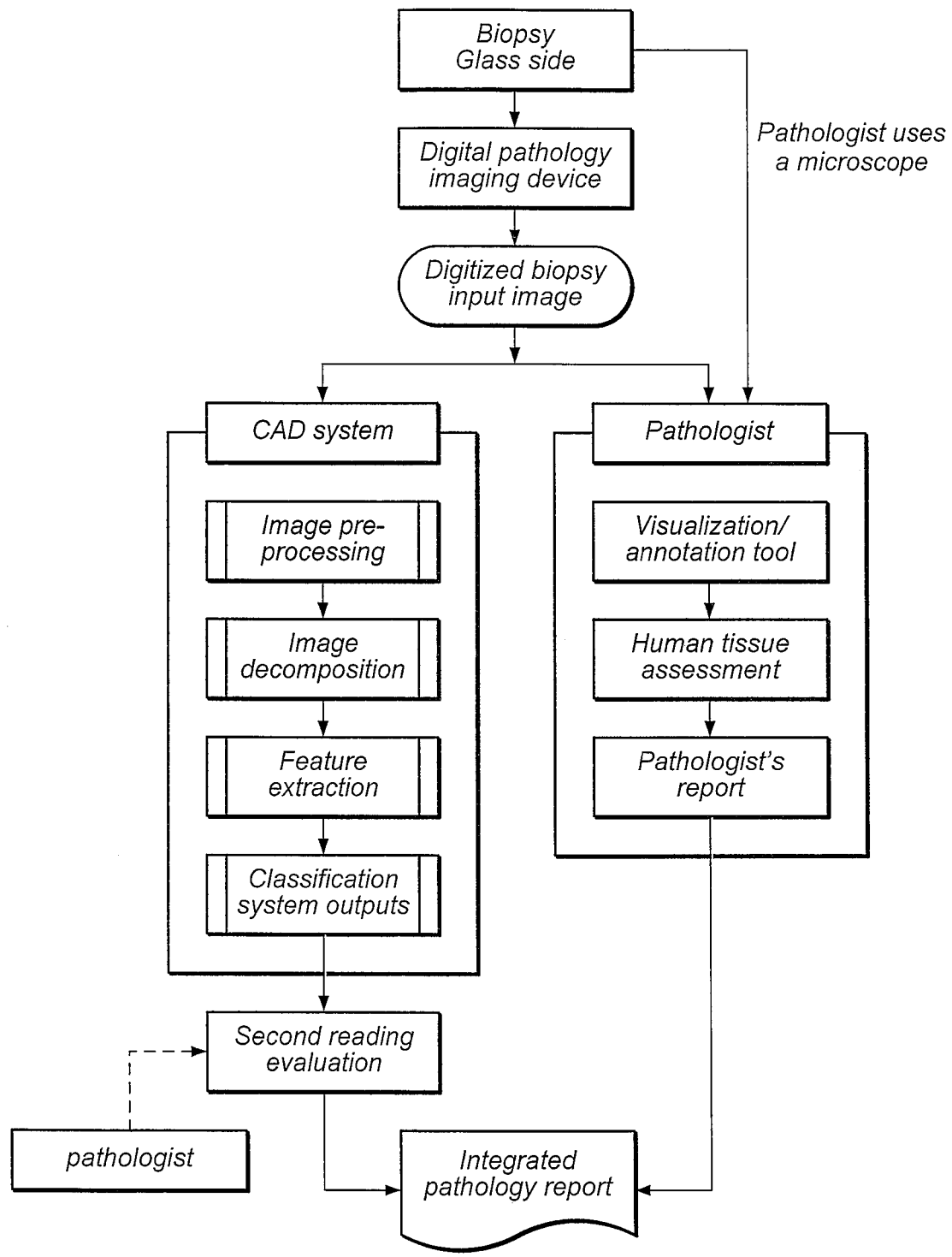
FIG. 8 is a functional block diagram showing an example of an assessment of histopathology images of the present invention.
Figure 9:
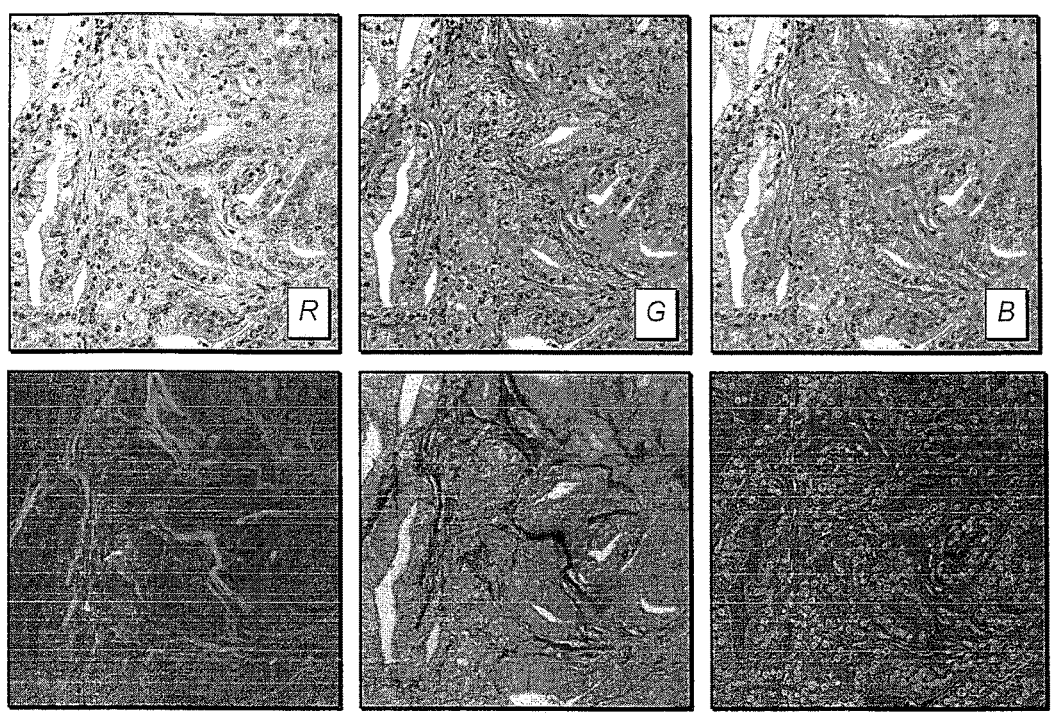
FIG. 9 depicts an exemplary logarithmic color model of prostate cancer images.

Another embodiment of the present invention discloses a method for producing an integrated pathology report, which contains information from visual assessment of biopsy tissue performed by an expert pathologist and quantitative information from automated computer-aided systems. This disclosure is presented in FIG. 8. The system is composed by two main components: (1) one or more pathologists and (2) one or more automated classification system. The input to the system consists of biopsy slides, which can be evaluated by a pathologist directly by using a microscope or other digital pathology imaging system. The pathologist may use a computer tool for image visualization or annotation and then generate a preliminary pathology report. In addition, an independent automated expert system performs the computerized analysis of the digitized version of the biopsy image. The results of the computer-aided diagnosis system (i.e. detected cancerous regions, cancer grade, localization, extent, area occupied by cancer, tumor volume, etc.), are treated as a second opinion and are presented to the human pathologist evaluation for approval. If the outcomes of the system are validated by a pathologist, the information from human and computer tissue assessment are integrated to produce a more complete and accurate pathology report. Any of the computer-aided diagnosis system may be utilized as the independent automated expert system.

It should be further noted that, with respect to all the of embodiments disclosed herein, the disclosed training and validation steps for the classifiers may occur at a different time and place than utilization of the classifiers to generate classes. This separate training of the system for future use also constitutes a separate embodiment(s).

The present invention which is described hereinbefore with reference to flowchart and/or block diagram illustrations of methods, systems, devices, simulations, and computer program products in accordance with some embodiments of the invention has been illustrated in detail by using a computer system. For instance, the flowchart and/or block diagrams further illustrate exemplary operations of the computer systems and methods of FIG. 1 to FIG. 8. It is also conceivable that each block of the flowchart and/or block diagram illustrations, and combinations of blocks in the flowchart and/or block diagram illustrations, may be implemented by any computer program instructions and/or hardware. These computer program instructions may be provided to a processor of a general purpose computer, a microprocessor, a portable device such as cell phones, a special purpose computer or device, or other programmable data processing apparatus to produce a device, such that the instructions, which execute via the processor of the computer or other programmable data processing apparatus, create means for implementing the functions specified in the flowcharts and/or block diagrams or blocks. The computer program may also be supplied from a remote source embodied in a carrier medium such as an electronic signal, including a radio frequency carrier wave or an optical carrier wave.

Further modifications and alternative embodiments of various aspects of the invention will be apparent to those skilled in the art in view of this description. Accordingly, this description is to be construed as illustrative only and is for the purpose of teaching those skilled in the art the general manner of carrying out the invention. It is to be understood that the forms of the invention shown and described herein are to be taken as examples of embodiments. Elements and materials may be substituted for those illustrated and described herein, parts and processes may be reversed, and certain features of the invention may be utilized independently, all as would be apparent to one skilled in the art after having the benefit of this description of the invention. Changes may be made in the elements described herein without departing from the spirit and scope of the invention as claimed.

What is claimed is:

1. A method for performing multi-stage classification for detection of cancer regions from one or more digitized images of biopsy slides comprising:
    pre-processing, from the digitized images, biopsy regions of interest or biopsy whole-slides, using color normalization methods and segmentation methods;
    decomposing the pre-processed digitized images into several segments;
    describing the image segments by forming feature vectors based on at least one of textural, color, or morphology tissue characteristics;
    classifying the image segments using one or more classification methods in a first classification stage, wherein the classification methods utilize the feature vectors of the image segments, and further wherein the classification methods are able to produce scores and posterior conditional probabilities or equivalents for each possible class, and further wherein the first classification stage is a multi-class classifier;
    classifying one or more of the image segments using a second classification stage if one or more conditions are met, wherein the second classification stage comprises a set of one or more specialized classifiers or refinement classifiers which are trained on a smaller group of classes with respect to the classifiers used in the first stage;
    classifying, based upon either the first or second classification stage, a portion of the region of interest or biopsy whole slides, as cancerous or non-cancerous;
    determining a cancer classification, tumor extent, tumor size, or tumor localization based at least in part upon the output of either of the first or second classification stage.

2. The method of claim 1, wherein the condition comprises when a maximum posterior probability produced in the first classification stage is less than a confidence threshold.

3. The method of claim 1, wherein the condition comprises when two or more of the classes outputted by the first classification stage have a difference in classification margin or when the two or more classes have similar posterior probabilities.

4. The method of claim 1, wherein the classification methods used in the second classification stage are binary.

5. The method of claim 1, wherein the digitized images comprise biopsy images of different body tissues.

6. The method of claim 1, wherein, for one or more of the classification methods used in either the first or second classification stage, data utilized by the classification methods for training or validation is separated into at least two disjoint groups using a cross-validation approach.

7. The method of claim 1, wherein image color normalization is performed by one or more of the following: fuzzy local color transference, color deconvolution, the Reinhard method, histogram matching, or non-linear color mapping.

8. The method of claim 1, where the preprocessed digitized images may be decomposed to generate various images' segments using: channel decomposition, bit plane decomposition, empirical mode decomposition, ensemble empirical mode decomposition, or human visual system-based image segmentation.

9. The method of claim 1, wherein at least one of one of the classifiers' parameters is adjusted using cross-validation based on the performance metrics obtained through several cross-validation rounds.

10. The method of claim 1, wherein at least one of the classification stages outputs posterior probabilities of Gleason grades, and the outputed posterior probabilities are used to estimate the distribution of grades within a tissue core.

11. A method for performing multi-stage classification for detection of cancer regions from one or more digitized images of biopsy slides comprising:
    pre-processing, from the digitized images, biopsy regions of interest or biopsy whole-slides, using color normalization methods and segmentation methods;
    decomposing the pre-processed digitized images into several segments;
    describing the image segments by forming feature vectors based on at least one of textural, color, or morphology tissue characteristics;
    classifying the image segments using one or more classification methods in a first classification stage, wherein the classification methods utilize the feature vectors of the image segments, and further wherein the classification methods are able to produce scores and posterior conditional probabilities or equivalents for each possible class;
    classifying one or more of the image segments using a second classification stage if one or more conditions are met;
    classifying, based upon either the first or second classification stage, a portion of the region of interest or biopsy whole slides, as cancerous or non-cancerous;
    determining a cancer classification, tumor extent, tumor size, or tumor localization based at least in part upon the output of either of the first or second classification stage;
    wherein at least one of the classification stages outputs posterior probabilities of Gleason grades, and the outputed posterior probabilities are used to estimate the distribution of grades within a tissue core.

12. The method of claim 11, wherein the condition comprises when the maximum posterior probability produced in the first classification stage is less than a confidence threshold.

13. The method of claim 11, wherein the condition comprises when two or more of the classes outputted by the first classification stage have a small difference in classification margin or when the two or more classes have similar posterior probabilities.

14. The method of claim 11, wherein the classification methods used in the second classification stage are binary.

15. The method of claim 11, wherein the digitized images comprise biopsy images of different body tissues.

16. The method of claim 11, wherein, for one or more of the classification methods used in either the first or second classification stage, data utilized by the classification methods for training or validation is separated into at least two disjoint groups using a cross-validation approach.

17. The method of claim 11, wherein image color normalization is performed by one or more of the following: fuzzy local color transference, color deconvolution, the Reinhard method, histogram matching, or non-linear color mapping.

18. The method of claim 11, where the preprocessed digitized images may be decomposed to generate various images' segments using: channel decomposition, bit plane decomposition, empirical mode decomposition, ensemble empirical mode decomposition, or human visual system-based image segmentation.

19. The method of claim 11, wherein at least one of one of the classifiers' parameters is adjusted using cross-validation based on the performance metrics obtained through several cross validation rounds.

* * * * *

UNITED STATES PATENT AND TRADEMARK OFFICE
CERTIFICATE OF CORRECTION

PATENT NO. : 10,055,551 B2
APPLICATION NO. : 15/028314
DATED : August 21, 2018
INVENTOR(S) : Agaian et al.

Page 1 of 1

It is certified that error appears in the above-identified patent and that said Letters Patent is hereby corrected as shown below:

On the Title Page

In the Assignee:
Please correct the Assignee to read "Board of Regents of the University of Texas System, Austin, TX (US) and The Board of Trustees of the Leland Stanford Junior University, Stanford, CA"

Signed and Sealed this
Sixteenth Day of July, 2019

Andrei Iancu
*Director of the United States Patent and Trademark Office*